(12) United States Patent
Schmidt

(10) Patent No.: US 10,688,309 B2
(45) Date of Patent: Jun. 23, 2020

(54) DOUBLE HELIX CONDUCTOR WITH WINDING AROUND CORE

(71) Applicant: Medical Energetics Limited, Galway (IE)

(72) Inventor: David G. Schmidt, San Diego, CA (US)

(73) Assignee: Medical Energetics Limited, Galway (IE)

( * ) Notice: Subject to any disclaimer, the term of this patent is extended or adjusted under 35 U.S.C. 154(b) by 307 days.

(21) Appl. No.: 15/866,410

(22) Filed: Jan. 9, 2018

(65) Prior Publication Data

US 2018/0126186 A1    May 10, 2018

Related U.S. Application Data

(63) Continuation of application No. 14/532,975, filed on Nov. 4, 2014, now Pat. No. 9,861,830.

(60) Provisional application No. 61/963,965, filed on Dec. 18, 2013.

(51) Int. Cl.

| | | |
|---|---|---|
| *A61N 2/02* | (2006.01) |
| *H01F 27/24* | (2006.01) |
| *H01F 27/28* | (2006.01) |
| *A61N 2/00* | (2006.01) |
| *A61N 1/40* | (2006.01) |

(52) U.S. Cl.
CPC ............... *A61N 2/02* (2013.01); *A61N 2/002* (2013.01); *H01F 27/24* (2013.01); *H01F 27/2823* (2013.01); *A61N 1/40* (2013.01)

(58) Field of Classification Search
CPC .......... A61N 2/008; A61N 2/002; A61N 2/02; A61N 1/40; H01F 5/00; H01F 27/2823; H01F 27/24
USPC ..... 600/9–14; 128/897–899; 336/65, 68, 73, 336/185, 199, 206, 208, 229; 47/1.3
See application file for complete search history.

(56) References Cited

U.S. PATENT DOCUMENTS

| | | |
|---|---|---|
| 1,898,661 A | 2/1933 | Hagen |
| 2,035,274 A | 3/1936 | Mougey |
| 2,297,454 A | 9/1942 | Berger |
| 2,850,666 A | 9/1958 | Brewer |
| 3,037,175 A * | 5/1962 | Ruthroff ................. H01F 19/06 333/32 |
| 3,066,295 A | 11/1962 | Krause et al. |
| 3,519,964 A | 7/1970 | Chorney |
| 3,588,689 A | 6/1971 | Crawford |
| 3,683,393 A | 8/1972 | Self |
| 3,760,812 A | 9/1973 | Timm et al. |
| 3,774,452 A | 11/1973 | Tullos et al. |
| 4,131,759 A | 12/1978 | Felkel |

(Continued)

FOREIGN PATENT DOCUMENTS

| | | |
|---|---|---|
| GB | 479841 | 2/1938 |
| GB | 2480610 | 11/2011 |

(Continued)

*Primary Examiner* — Navin Natnithithadha
*Assistant Examiner* — Sunita Reddy
(74) *Attorney, Agent, or Firm* — Arc IP Law, PC; Joseph J. Mayo

(57) ABSTRACT

An electrical system including a body having a structure resembling a double helix wound around a toroidal structure may be used to produce useful electromagnetic effects for various applications, including providing therapy and promoting growth of living organisms.

20 Claims, 16 Drawing Sheets

(56) References Cited

U.S. PATENT DOCUMENTS

| | | | |
|---|---|---|---|
| 4,229,676 A | 10/1980 | Manely | |
| 4,242,651 A * | 12/1980 | Dutta Roy | H03H 7/38 333/32 |
| 4,266,532 A | 5/1981 | Ryaby et al. | |
| 4,439,702 A | 3/1984 | Belikov et al. | |
| 4,489,276 A | 12/1984 | Yu | |
| 4,749,420 A * | 6/1988 | Phillips | H01R 43/005 156/245 |
| 4,832,051 A | 5/1989 | Jarvik et al. | |
| 4,989,617 A | 2/1991 | Memberg et al. | |
| 5,077,934 A | 1/1992 | Liboff et al. | |
| 5,079,458 A | 1/1992 | Schuster | |
| 5,173,669 A | 12/1992 | Manoly | |
| 5,182,537 A | 1/1993 | Thuis | |
| 5,339,061 A | 8/1994 | Reick | |
| 5,359,340 A | 10/1994 | Yokota | |
| 5,366,493 A | 11/1994 | Scheiner et al. | |
| 5,464,456 A | 11/1995 | Kertz | |
| 5,654,723 A | 8/1997 | Craven et al. | |
| 5,819,467 A | 10/1998 | Zucker | |
| 5,851,206 A * | 12/1998 | Guglielmi | A61B 17/12022 606/28 |
| 5,892,480 A | 4/1999 | Killen | |
| 5,909,165 A | 6/1999 | Leupold | |
| 5,954,630 A | 9/1999 | Masaki et al. | |
| 5,977,932 A | 11/1999 | Robinson | |
| 6,005,462 A | 12/1999 | Myers | |
| 6,159,206 A * | 12/2000 | Ogawa | A61B 17/12022 606/29 |
| 6,169,523 B1 | 1/2001 | Ploussios | |
| 6,239,760 B1 | 5/2001 | Voorhies | |
| 6,300,920 B1 | 10/2001 | Pertl et al. | |
| 6,520,986 B2 | 2/2003 | Martin | |
| 6,552,530 B1 * | 4/2003 | Vaiser | H01Q 7/00 324/204 |
| 6,593,900 B1 * | 7/2003 | Craven | H01Q 1/38 343/742 |
| 6,770,023 B2 | 8/2004 | Vaiser et al. | |
| 6,921,042 B1 | 7/2005 | Goodzeit et al. | |
| 6,978,179 B1 | 12/2005 | Flagg | |
| 7,148,783 B2 | 12/2006 | Parsche et al. | |
| 7,154,368 B2 | 12/2006 | Sweeney et al. | |
| 7,375,449 B2 | 5/2008 | Butterfield | |
| 8,323,328 B2 | 12/2012 | Martin | |
| 8,463,407 B2 | 6/2013 | Bulkes et al. | |
| 8,652,023 B2 | 2/2014 | Schmidt | |
| 8,653,925 B2 | 2/2014 | Schmidt | |
| 8,749,333 B2 | 6/2014 | Schmidt | |
| 8,919,035 B2 | 12/2014 | Schmidt | |
| 8,961,384 B2 | 2/2015 | Schmidt | |
| 9,030,283 B2 | 5/2015 | Schmidt | |
| D740,760 S * | 10/2015 | Gliksman | D13/153 |
| 9,370,667 B2 | 6/2016 | Schmidt | |
| 9,406,421 B2 | 8/2016 | Schmidt | |
| 9,504,845 B2 | 11/2016 | Schmidt | |
| 2003/0011527 A1 | 1/2003 | Kokorin et al. | |
| 2003/0095022 A1 | 5/2003 | Boynton | |
| 2003/0158585 A1 | 8/2003 | Burnett | |
| 2003/0169132 A1 | 9/2003 | Vaiser et al. | |
| 2003/0230427 A1 * | 12/2003 | Gareis | H01B 11/04 174/113 C |
| 2004/0008153 A1 * | 1/2004 | Lamensdorf | H01Q 1/362 343/895 |
| 2004/0093022 A9 * | 5/2004 | Kurz | A61B 17/12022 606/213 |
| 2005/0094989 A1 | 5/2005 | Halpin | |
| 2005/0121396 A1 | 6/2005 | Kosakewich | |
| 2005/0228209 A1 | 10/2005 | Schneider et al. | |
| 2007/0024520 A1 | 2/2007 | Preble | |
| 2007/0167990 A1 | 7/2007 | Mangrum et al. | |
| 2007/0258329 A1 | 11/2007 | Winey | |
| 2008/0161884 A1 | 7/2008 | Chandler et al. | |
| 2008/0266203 A1 | 10/2008 | Rossetto et al. | |
| 2008/0306325 A1 | 12/2008 | Burnett et al. | |
| 2009/0083969 A1 | 4/2009 | Meinke | |
| 2009/0206974 A1 | 8/2009 | Meinke | |
| 2009/0260849 A1 | 10/2009 | Cardas | |
| 2010/0005711 A1 | 1/2010 | McNeff | |
| 2010/0057655 A1 | 3/2010 | Jacobson et al. | |
| 2010/0113862 A1 | 5/2010 | Kotowich | |
| 2010/0114280 A1 * | 5/2010 | Hill | A61N 1/0573 607/116 |
| 2010/0121131 A1 | 5/2010 | Mathes | |
| 2010/0152811 A1 | 6/2010 | Flaherty | |
| 2010/0160713 A1 | 6/2010 | Cuppen | |
| 2010/0179630 A1 | 7/2010 | Williams | |
| 2010/0185041 A1 | 7/2010 | Lee | |
| 2012/0101366 A1 | 4/2012 | Ruohonen | |
| 2012/0143285 A1 | 6/2012 | Wang | |
| 2012/0223800 A1 | 9/2012 | Schmidt | |
| 2013/0131537 A1 * | 5/2013 | Tam | A61B 5/4854 600/544 |
| 2013/0192129 A1 | 8/2013 | Schmidt | |
| 2013/0211181 A1 | 8/2013 | Schmidt | |
| 2013/0274542 A1 | 10/2013 | Volo | |
| 2013/0285782 A1 | 10/2013 | Schmidt | |
| 2014/0097925 A1 | 4/2014 | Schmidt | |
| 2014/0100412 A1 | 4/2014 | Schmidt | |
| 2014/0218149 A1 | 8/2014 | Schmidt | |
| 2014/0371514 A1 | 12/2014 | Schmidt | |
| 2015/0119630 A1 | 4/2015 | Schmidt | |
| 2015/0119631 A1 | 4/2015 | Schmidt | |
| 2015/0119632 A1 | 4/2015 | Schmidt | |
| 2015/0157871 A1 | 6/2015 | Schmidt | |
| 2015/0283393 A1 | 10/2015 | Schmidt | |
| 2015/0283394 A1 | 10/2015 | Schmidt | |
| 2016/0172088 A1 | 6/2016 | Schmidt | |
| 2016/0172101 A1 | 6/2016 | Schmidt | |
| 2016/0247614 A1 | 8/2016 | Schmidt | |
| 2016/0247617 A1 | 8/2016 | Schmidt | |
| 2016/0365186 A1 | 12/2016 | Schmidt | |

FOREIGN PATENT DOCUMENTS

| | | |
|---|---|---|
| WO | 2012/118971 | 9/2012 |
| WO | 2013/112810 | 8/2013 |
| WO | 2013/123009 | 8/2013 |

* cited by examiner

DOUBLE HELIX CONDUCTOR WITH WINDING AROUND CORE

This patent application is a continuation of U.S. patent application Ser. No. 14/532,975, issued as U.S. Pat. No. 9,861,830, filed on 4 Nov. 2014, which claims the benefit of U.S. Provisional Patent Application Ser. No. 61/963,965, filed on 18 Dec. 2013, the specifications of which are hereby incorporated herein by reference.

BACKGROUND OF THE INVENTION

Field of the Invention

The invention relates to bodies including helically wound runners that form a double helix around a toroidal structure, devices including such bodies, and/or (electrical) systems including such bodies that are configured to generate electromagnetic effects. The invention further relates to the manufacture of such bodies, devices, and/or systems. The invention further relates to methods of operation of such devices and systems, and applications thereof. The invention further relates to such devices and/or systems configured to provide therapy to patients or promote growth of living organisms by using the generated electromagnetic effects.

Description of the Related Art

Spirally wound electrical conductors may exhibit certain electromagnetic properties and/or electromagnetic effects. For example, an electromagnetic coil may act as an inductor and/or part of a transformer, and has many established useful applications in electrical circuits. One or more electromagnetic coils may be used to exploit an electromagnetic field and/or other electromagnetic effect that is created when, e.g., one or more active current sources are operatively coupled to the one or more coils.

BRIEF SUMMARY OF THE INVENTION

One aspect of the invention relates to a system comprising one or more bodies, one or more current sources, one or more conductive wires, and/or other components. Individual bodies may include two intertwined helically wound runners. A first runner may be coupled to the second runner, e.g. by struts. Individual runners may have a helical shape. Two runners may be arranged to form a double helix. The double helix may be arranged around a toroidal structure. For example, a toroidal structure may be the same as or similar to a torus. Individual bodies may be arranged in a circular shape, a toroidal shape, and/or other shapes. One or more conductive wires may be spirally wound around one or more of a first runner, a second runner, and the toroidal structure. One or more runners may be configured to conduct current and/or emit electromagnetic radiation.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION OF THE INVENTION

Figure 15:
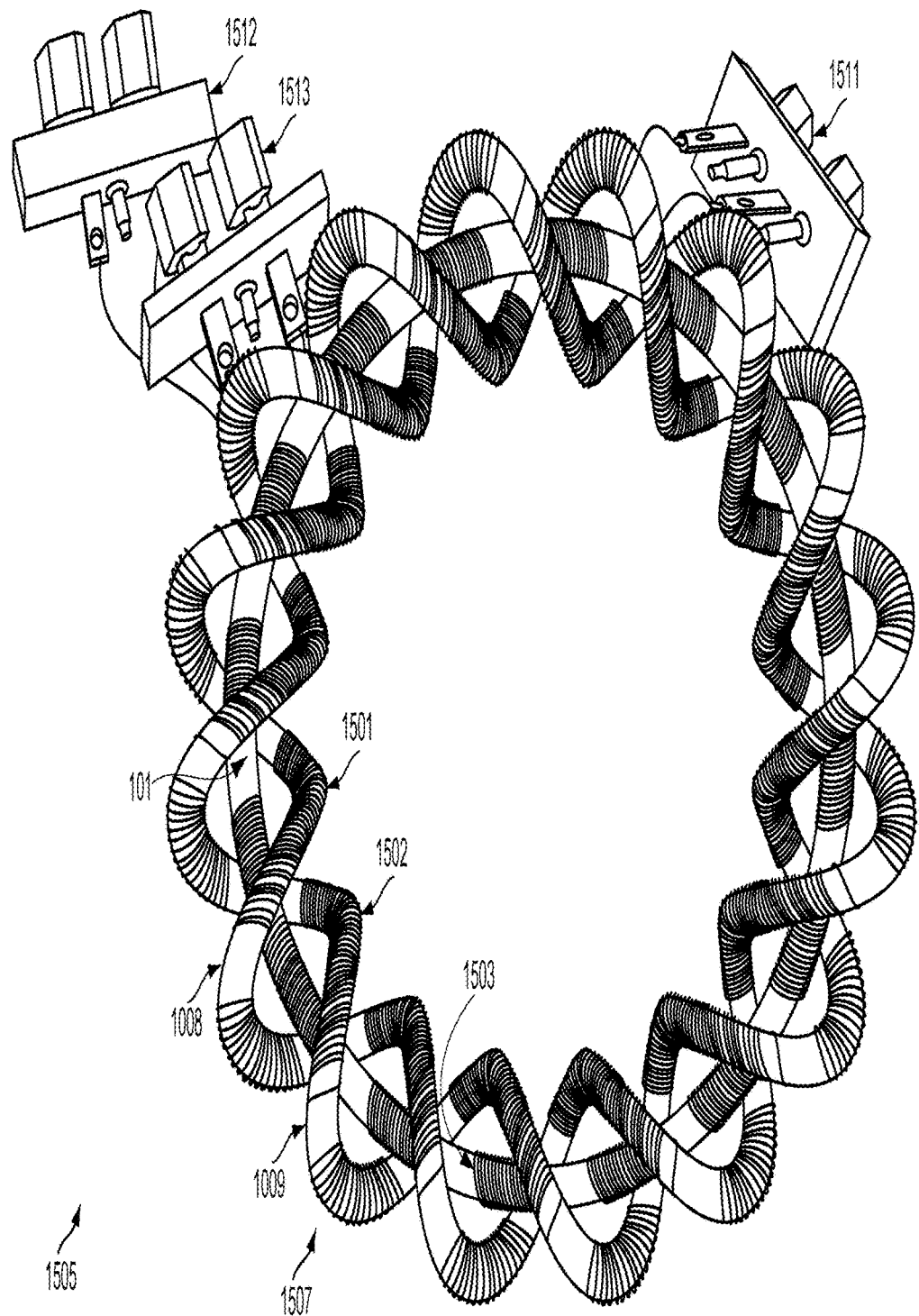
FIG. 15 illustrates a top-down view of an exemplary system combining a body that includes a toroidal structure within a double helix.

FIG. 15 illustrates a top-down view of an exemplary body 1507 that includes a first runner 1008 and a second runner 1009 helically wound around a toroidal structure 101 to form a system 1505 configured to provide therapy and/or electromagnetic effects to living organisms and/or subjects. FIGS. 1-10, 11A, and 11B illustrate how to form body 1507 and variations thereof.

Figure 1:
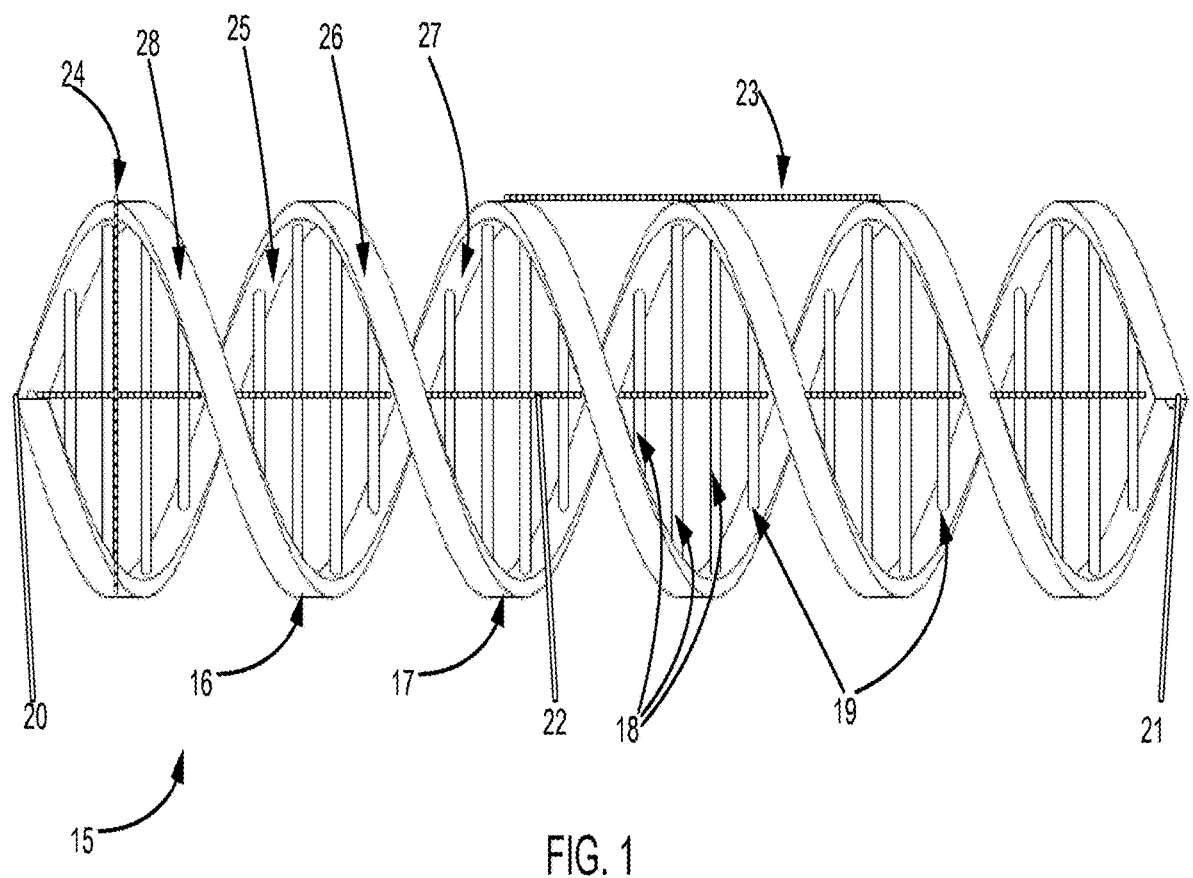
FIG. 1 illustrates a side view of an exemplary body including two intertwined helically wound runners, coupled by struts.

FIG. 1 illustrates a side view of an exemplary body 15. Body 15 may include two or more intertwined helically wound runners runner 16 and runner 17. Runner 16 and runner 17 may be coupled by struts 18, shown at 19 for example. Body 15 includes two ends end 20 and end 21—disposed at opposite sides of body 15. Runners 16 and/or 17 may be arranged in the shape of a three-dimensional curve similar to or substantially the same as a helix and/or double helix. A helix may be characterized by the fact that a tangent line at any point along the curve has a constant angle with a (fixed) line called the axis. The pitch of a helix may be the width of one 360 degree helix turn (a.k.a. revolution), e.g. measured parallel to the axis of the helix. Intertwined helically wound runners may share the same axis, be congruent, and/or differ by a translation along the axis, e.g. measuring half the pitch. The two runners shown in FIG. 1 may share the same axis 22, extending horizontally for approximately three complete revolutions. Runner 16 and runner 17 may form a double helix. The length of body 15, as measured along axis 22 from end 20 to end 21, may thus be approximately three times the length of pitch 23. A helical shape may have constant pitch, constant radius (measured in the plane perpendicular to the axis), constant torsion, constant curvature, constant ratio of curvature to torsion, and/or a straight axis. In FIG. 1, the radius of body 15 may be half of diameter 24. It is noted that the shape of body 15 resembles the general shape of deoxyribonucleic acid (DNA), e.g. a double helix.

By way of non-limiting example, additional structures and/or features of body 15 may be described in U.S. Pat. No. 8,653,925, entitled "Double Helix Conductor," which issued Feb. 18, 2014, which is hereby incorporated into this disclosure by reference in its entirety. This patent may also be referred to as "the '925 patent" herein.

In FIG. 1, the shape of cross-section of runner 16 and runner 17 may be a rectangle that is approximately three times wider than it is tall. Furthermore, the width of runner 16 or runner 17 may be approximately $1/13^{th}$ of the pitch of said runner of body 15. As a result, runner 17 of body 15 resembles a ribbon having an inner surface 25 (facing axis 22 of the helical shape) and an outer surface 26 (facing the opposite way as inner surface 25). Runner 16 of body 15 resembles a ribbon having an inner surface 27 (facing axis 22 of the helical shape) and an outer surface 28 (facing the opposite way as inner surface 27). Note that implementations of this disclosure are not intended to be limited by any of the given examples.

Runner 16, runner 17 and/or struts 18 may be manufactured from one or more of plastic, plastic plated with metals including copper, nickel, iron, soft iron, nickel alloys, fiberoptic materials, and/or other materials. In some implementations, runner 16, runner 17 and struts 18 are manufactured from non-conductive material. Runner 16, runner 17, and/or struts 18 may be manufactured from different materials. In some implementations, runner 16, runner 17 and/or struts 18 may include material that is flexible.

Runner 16, runner 17, and/or struts 18 may be manufactured through integral construction or formed separately prior to being assembled. In some implementations, runner 16, runner 17, and/or struts 18 may be include magnetically permeable material. In some implementations, runner 16, runner 17, and/or struts 18 may be include non-ferromagnetic yet conducting material.

Figure 2:
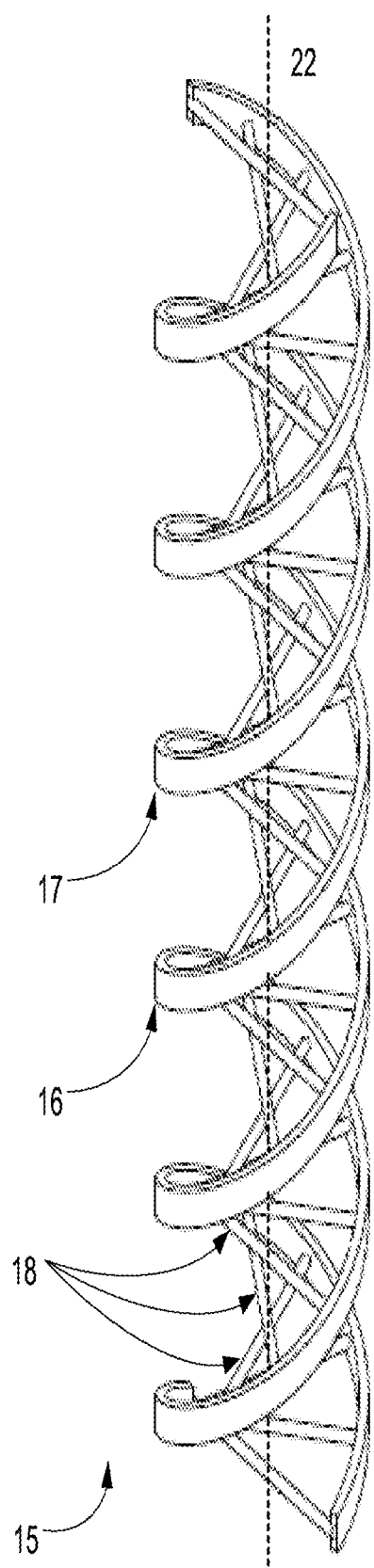
FIG. 2 illustrates an isometric view of an exemplary body including two intertwined helically wound runners, coupled by struts.

FIG. 2 illustrates an isometric view of an exemplary body 15 including two intertwined helically wound runners—runner 16 and runner 17—coupled by struts 18. Body 15 is shown here with axis 22 of both helically wound runners extending vertically.

Figure 3:
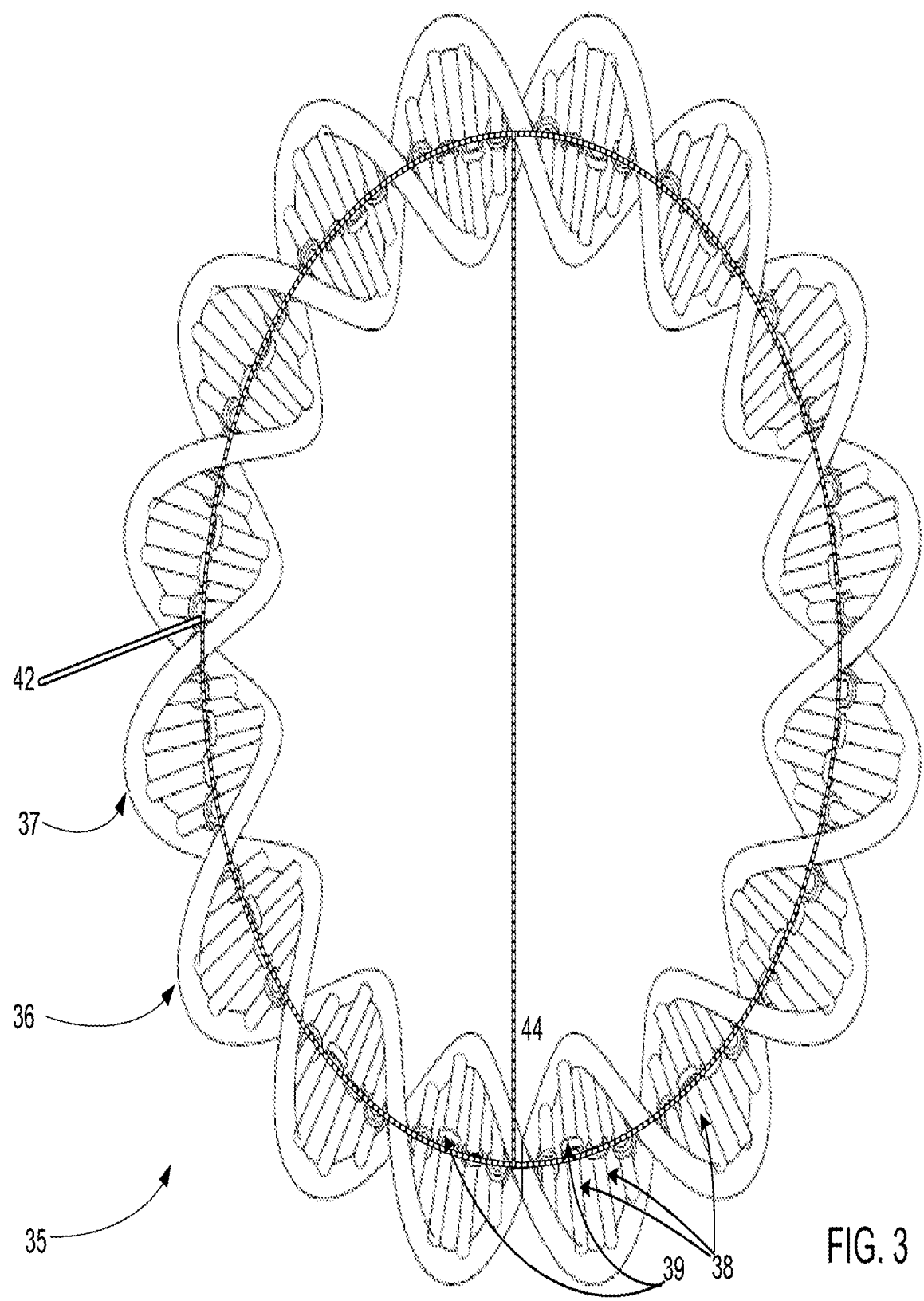
FIG. 3 illustrates a top-down view of an exemplary body including two intertwined helically wound runners sharing the same circular axis, both runners coupled by struts.

FIG. 3 illustrates a top-down view of an exemplary body 35 including two intertwined helically wound runners—runner 36 and runner 37—sharing the same circular axis 42, both runners coupled by struts 38. The resulting shape of body 35 may be referred to as toroidal. Body 35 may be formed the same as or similar to body 15, though comprising more revolutions, by arranging the body in a planar circular shape and joining both ends—end 20 and end 21 in FIG. 1—together. The preceding statement is not intended to limit the (process of) manufacture of bodies similar to or substantially the same as body 35 in any way.

Referring to FIG. 3, the diameter 44 of the circular axis of body 35, as well as the number of complete revolutions per runner required to completely extend along the entire circular axis 42 may be characteristic measurements/features of body 35. For example, as shown in FIG. 3, runner 36 and runner 37 of body 35 may require approximately eight complete revolutions around circular axis 42 to completely extend along the entire circular axis 42 of body 35, or some other number of rotations.

Note that one or more struts 38 of body 35 in FIG. 3 include a center-strut element 39, which is lacking from struts 18 of body 15. Center-strut element 39 may be associated with a particular strut of body 35. In some implementations, runners 36 and 37 as depicted in FIG. 3 may share one or more features attributed to runners 16 and 17 in FIGS. 1 and 2.

Figure 4:
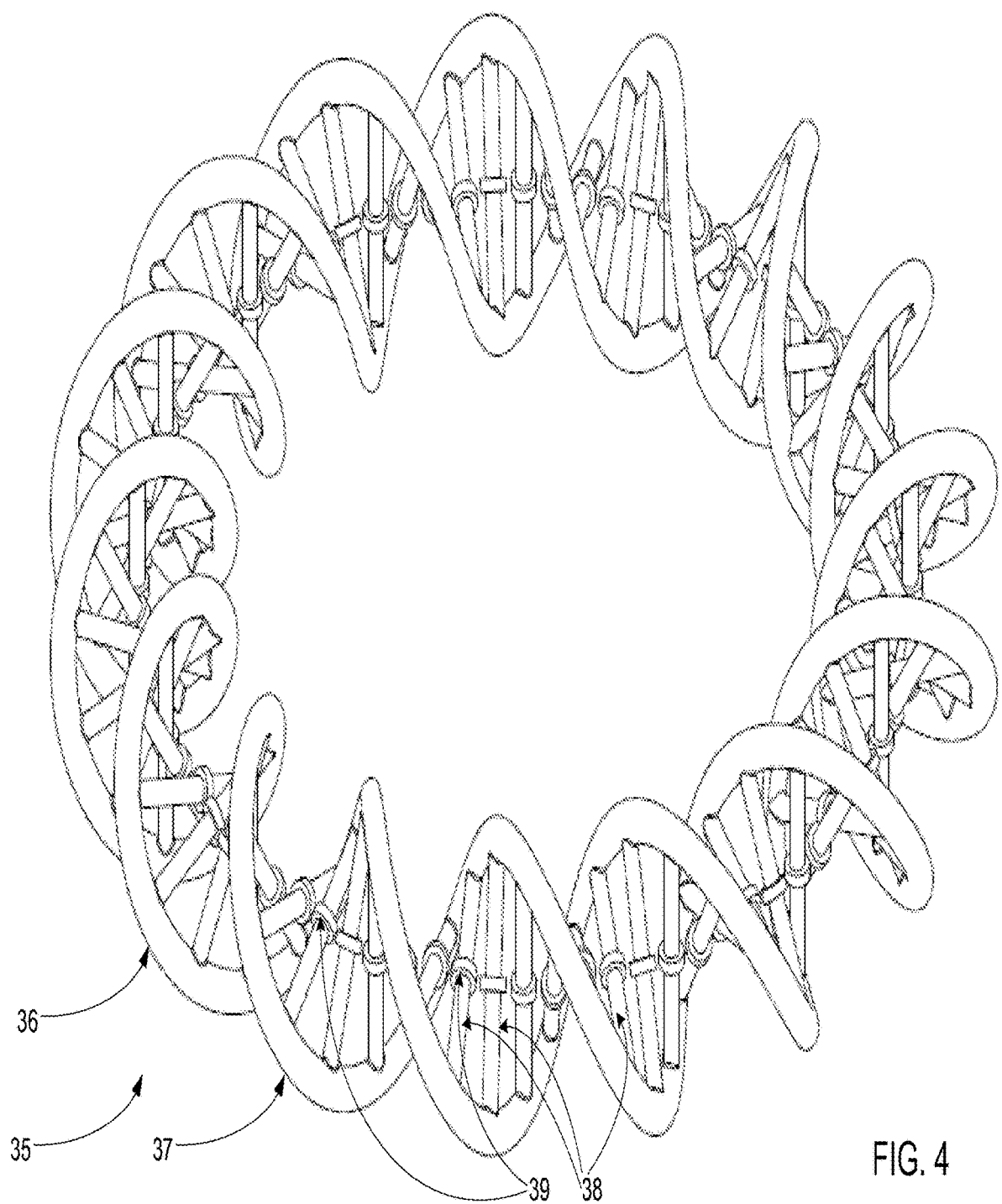
FIG. 4 illustrates an isometric view of an exemplary body including two intertwined helically wound runners sharing the same circular axis, both runners coupled by struts.

FIG. 4 illustrates an isometric view of an exemplary body 35 including two intertwined helically wound runners—runner 36 and runner 37—sharing the same circular axis, both runners coupled by struts 38. Note that, as in FIG. 3, the struts of body 35 in FIG. 4 may include a center-strut element 39, which may be lacking from struts 18 of body 15.

Figure 5:
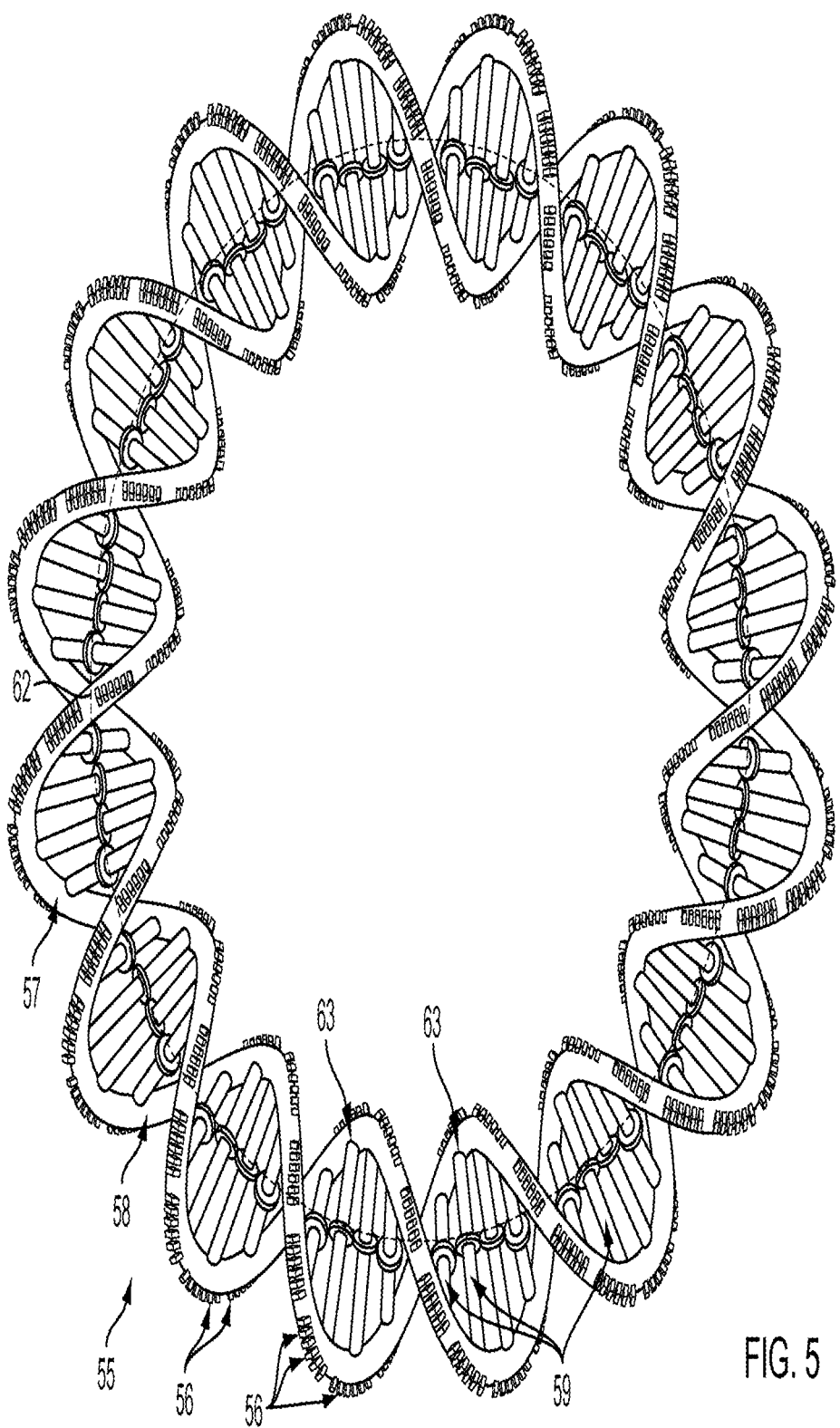
FIG. 5 illustrates a top-down view of an exemplary body including two intertwined helically wound runners sharing the same circular axis and having wire guides, both runners coupled by struts.

FIG. 5 illustrates a top-down view of an exemplary body 55 including two intertwined helically wound runners—runner 57 and runner 58—sharing the same circular axis 62 and having wire guides 56, both runners coupled by struts 59, shown at 63 for example. Any part of runner 57 or runner 58 may include wire guides 56. Wire guides 56 may include grooves, notches, protrusions, slots, and/or other structural elements disposed on and/or in runner 57 or runner 58 and configured to guide a wire along at least a part of the surface of runner 57 or runner 58.

Such a wire, as any wire listed in any figure included in this description, may be insulated, uninsulated, or partially insulated and partially uninsulated. As used herein, a "wire" may include a set of twisted wires (which may interchangeably be referred to as a "twisted wire"), including but not limited to a set of two twisted wires. The number of turns of a set of twisted wires per inch and/or per helical revolution of a runner may be characteristic measurements/features of the system. In some implementations, the number of twists per inch of a twisted wire may be about 2, about 5, about 10, about 20, about 100, and/or another suitable number of twists. In some implementations, the frequency characteristics of an alternating current and/or the corresponding generated electromagnetic field may be based on, proportional to, and/or otherwise related to the number of twists of a twisted wire. For example, a higher number of twists per inch may correspond to a higher operating frequency for the alternating current and/or the corresponding generated electromagnetic effect and/or field. In some implementations, multiple twisted wires (e.g. a first twisted wire wound around a first runner and a second twisted wire wound around a second runner) may have the same direction of twisting, and/or a different direction of twisting. In some implementations, multiple wires (e.g. twisted wires) may be wound around the same runner. In some implementations, a wire may be wound around some or all of one or more struts.

Figure 6:
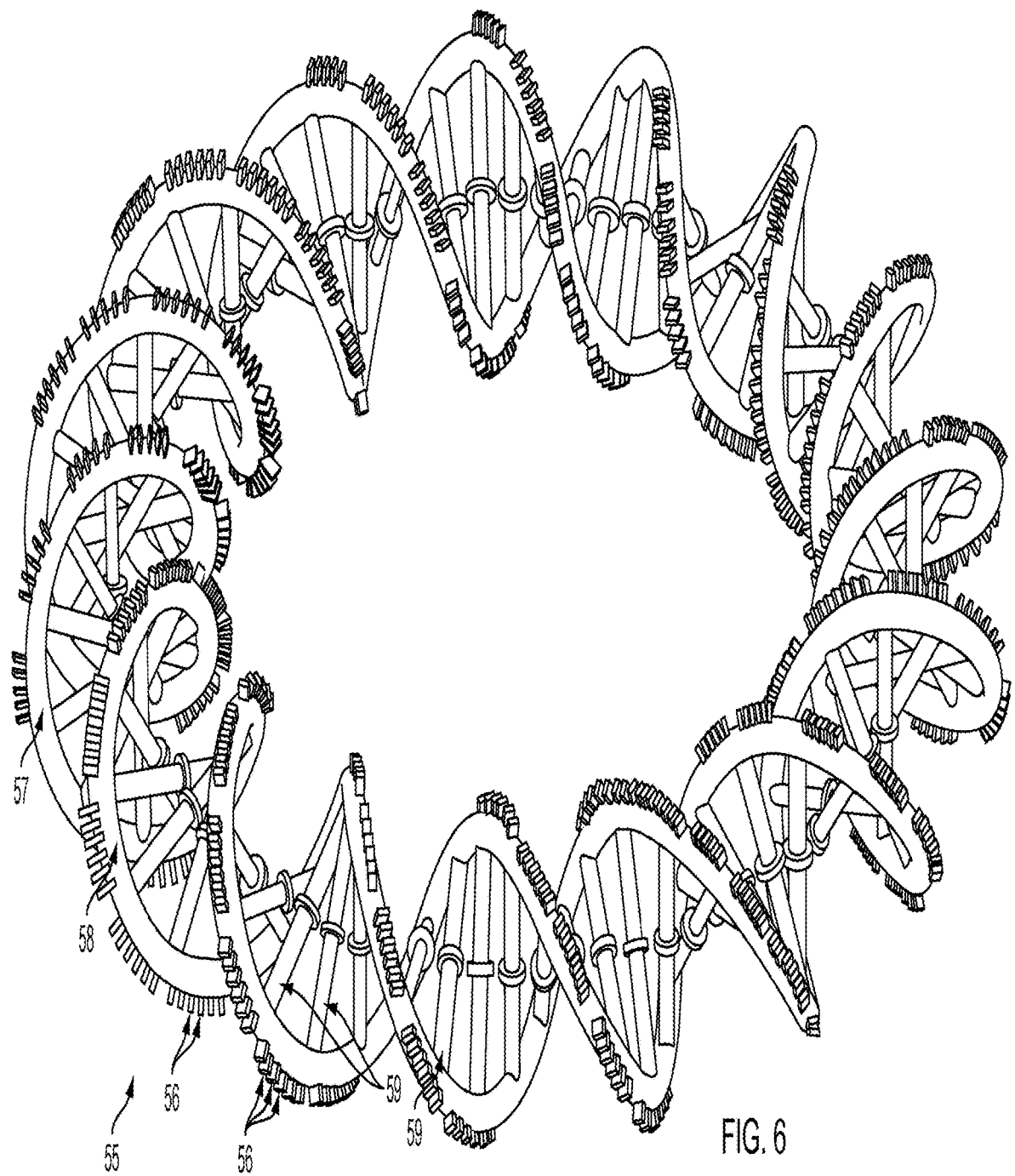
FIG. 6 illustrates an isometric view of an exemplary body including two intertwined helically wound runners sharing the same circular axis and having wire guides, both runner coupled by struts.

FIG. 6 illustrates an isometric view of an exemplary body 55 including two intertwined helically wound runners—runner 57 and runner 58—sharing the same circular axis and having wire guides 56, both runners coupled by struts 59.

Figure 7:
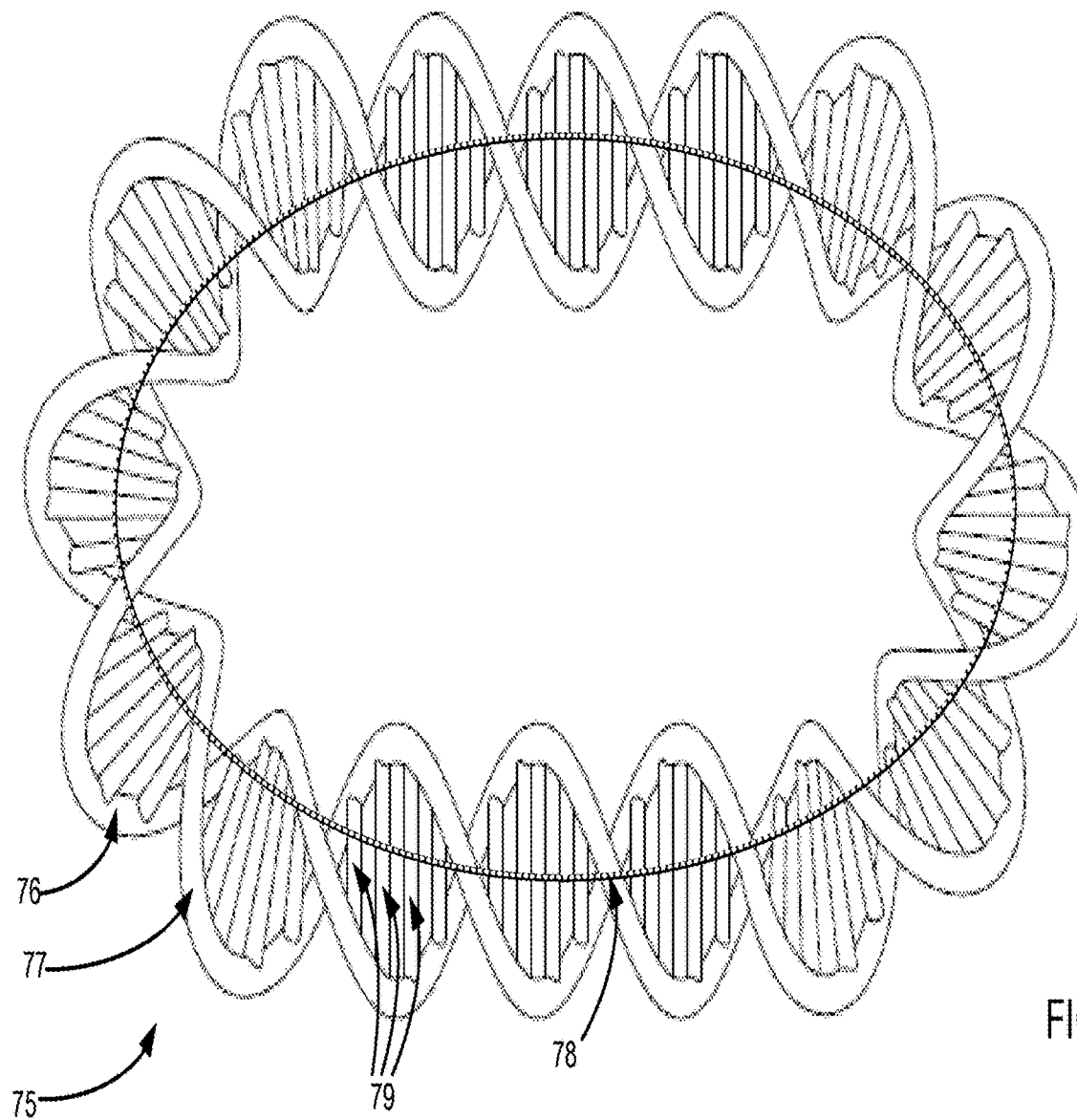
FIG. 7 illustrates an exemplary body including two intertwined helically wound runners sharing the same elliptical axis, both runner coupled by struts.

FIG. 7 illustrates an exemplary body 75 including two intertwined helically wound runners—runner 76 and runner 77—sharing the same elliptical axis 78, both runner coupled by struts 79. A body including two (or more) intertwined helically wound runners sharing the same axis may be arranged in any planar shape, including a circle, an oval, a triangle, a square, a rectangle, an angular shape, a polygon, and/or other planar shapes. Alternatively, and/or simultaneously, such a body may be arranged in a three-dimensional curve (a.k.a. space curve). In FIG. 7, body 75 may be formed from a body similar to body 15, though comprising more revolutions, by arranging the body in a planar elliptical shape and joining both ends—end 20 and end 21 in FIG. 1—together. The preceding statement is not intended to limit the (process of) manufacture of bodies similar to or substantially the same as body 75 in any way.

In some implementations, runners 76 and 77 as depicted in FIG. 7 may share one or more features attributed to runners 16 and 17 in FIGS. 1 and 2, and/or runners 36 and 37 in FIGS. 3 and 4. For example, runners 76 and 77 in FIG. 7 may include material that is flexible.

Figure 8:
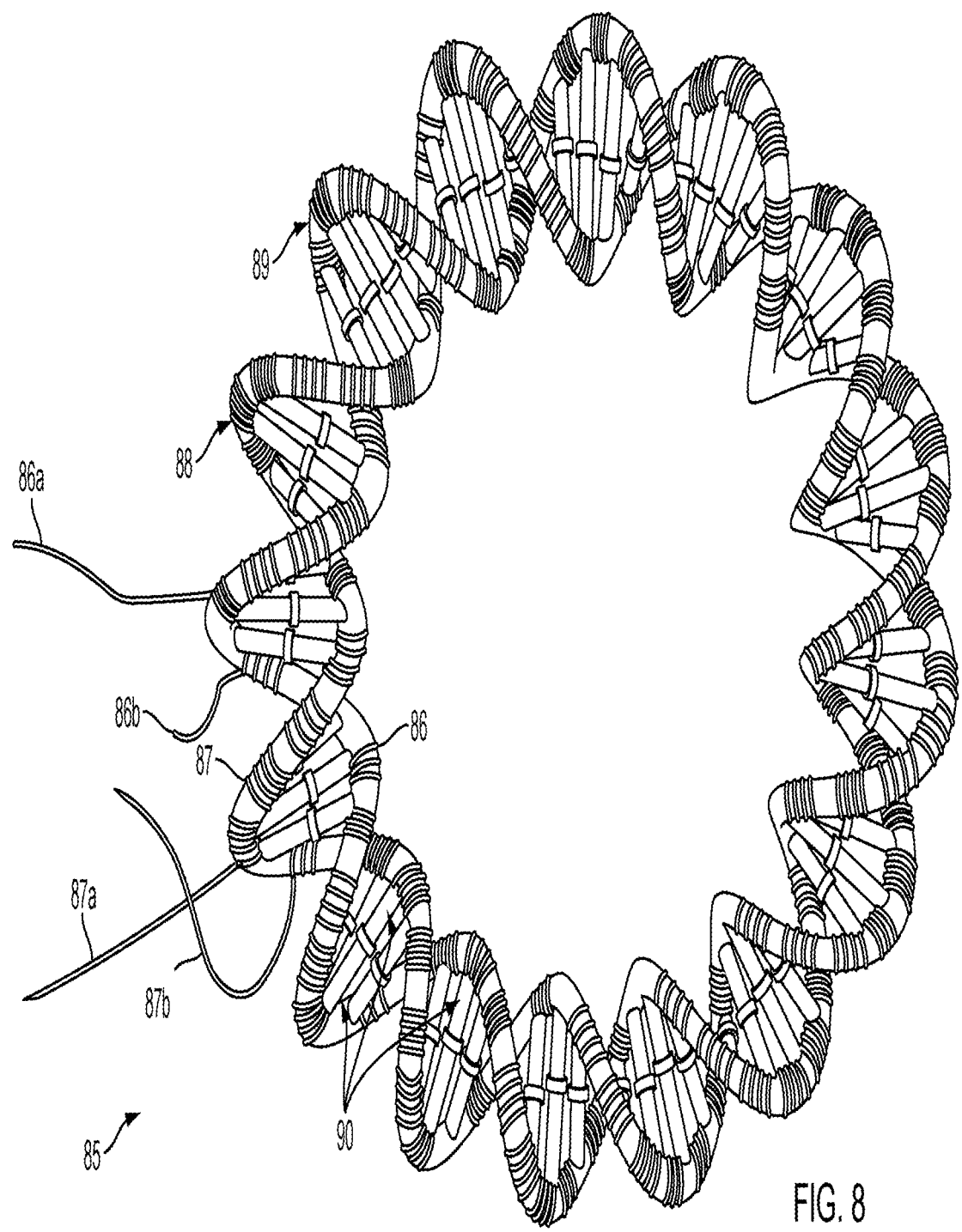
FIG. 8 illustrates a top-down view of an exemplary body including two intertwined helically wound runners sharing the same circular axis, both runners coupled by struts and having conductive wires spirally wound therearound.

FIG. 8 illustrates a top-down view of an exemplary body 85 including two intertwined helically wound runners—runner 88 and runner 89—sharing the same circular axis, coupled by struts 90 and having wires—wire 86 and wire 87—spirally wound therearound. In some implementations, wire 86 and/or wire 87 may be conductive wires. Wire 86 and/or wire 87, as any wire listed in any figure included in this description, may be insulated, uninsulated, or partially insulated and partially uninsulated. Wire 86 and/or wire 87, as any wire listed in any figure included in this description, may be a twisted wire. Runner 88 and runner 89 of body 85 may form cores around which wire 86 and wire 87 are spirally wound, respectively. As such, wire 86 and wire 87 may be arranged in a helical shape having axes that coincide with runner 88 and runner 89, respectively.

In some implementations, runners 88 and 89 as depicted in FIG. 8 may share one or more features attributed to runners 16 and 17 in FIGS. 1 and 2, and/or runners 36 and 37 in FIGS. 3 and 4, and/or runners 76 and 77 in FIG. 7. For example, in some implementations, runners 88 and/or 89 may include flexible material.

Wire 86 may include two leads—lead 86a and lead 86b. Wire 87 may include two leads—lead 87a and lead 87b. Wire 86 and wire 87 may be conductive. One or more bodies similar to or the same as body 85 may be used in an electrical system having one or more power sources and/or current sources arranged such that electrical coupling with one or both of wire 86 and wire 87 may be established, e.g. through coupling with lead 86a and 86b of wire 86 and through coupling with lead 87a and 87b of wire 87. The current supplied to wire 86 may be a direct current or an alternating current. The current supplied to wire 87 may be a direct current or an alternating current. The currents supplied to wire 86 and wire 87 may flow in the same direction or the opposite direction. For alternating currents, operating frequencies ranging from 0 Hz to 40 GHz are contemplated. The operating frequencies for wire 86 and wire 87 may be the same or different. Other electrical operating characteristics of current supplied to wire 86 and wire 87, such as phase, amplitude, power-level, and/or other operating characteristics, may be the same or different. The electrical system may be used to exploit the electromagnetic field that is created when electrical power is supplied to one or more wires of one or more bodies similar to or the same as body 85.

Figure 9:
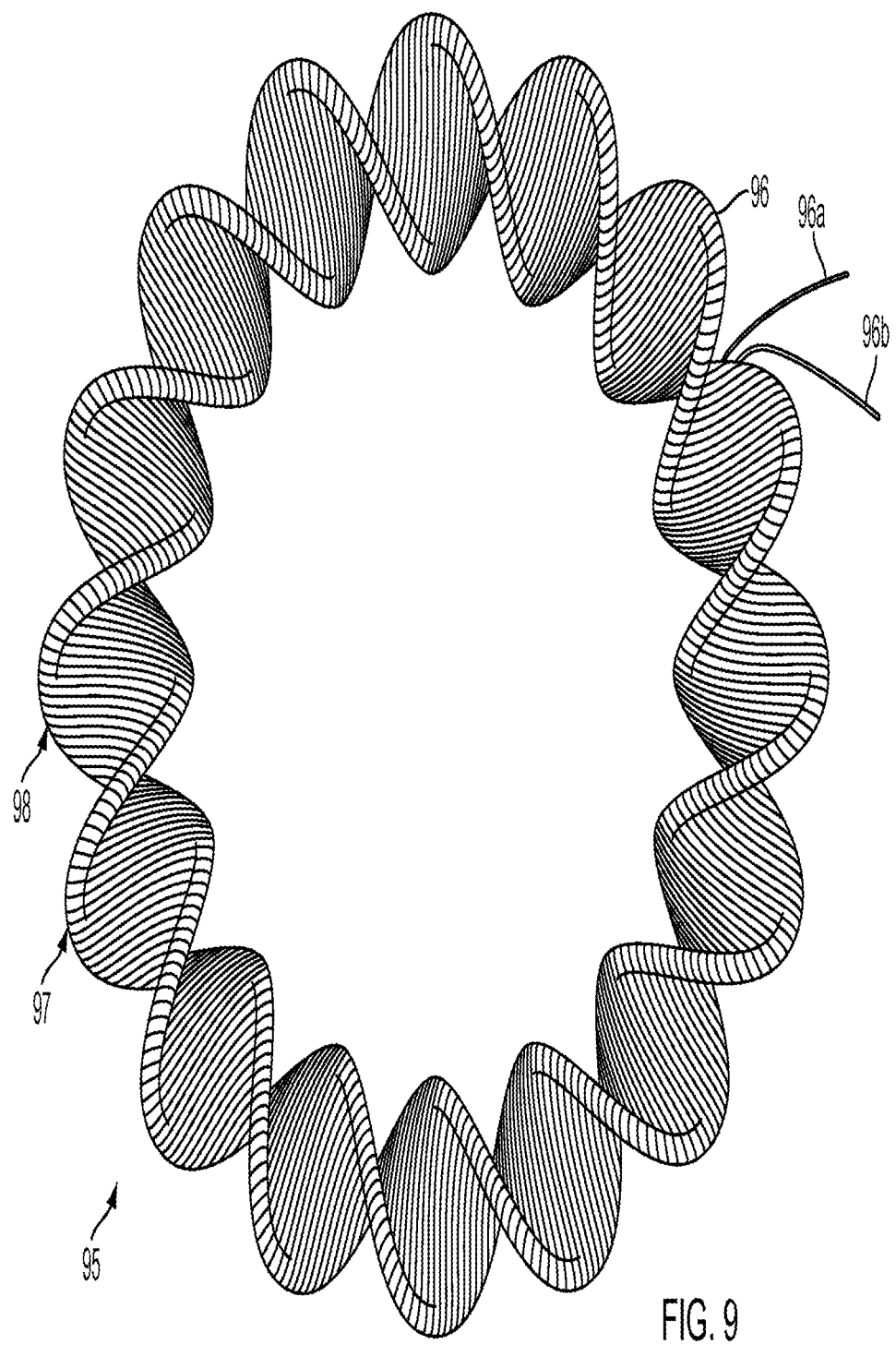
FIG. 9 illustrates a top-down view of an exemplary body including two intertwined helically wound runners sharing the same circular axis, both runner coupled by struts and having a wire spirally wound around both runners of the body.

FIG. 9 illustrates a top-down view of an exemplary body 95 including two intertwined helically wound runners—runner 97 and runner 98—sharing the same circular axis, both runner coupled by struts and having a wire 96 spirally wound around both runners of body 95. Wire 96 may include two leads—lead 86a and lead 86b. The resulting shape of body 95 with wire 96 may be referred to as a helicoidal shape. One or more bodies similar to or the same as body 95 may be used in an electrical system having a power source and/or a current source arranged such that electrical coupling with wire 96, e.g. through leads 96a and 96b, may be established. The electrical power supplied to wire 96 may include a direct current or an alternating current. Operating frequencies for an alternating current flowing through wire 96 are contemplated to range from 0 Hz to 40 GHz. The electrical system may be used to exploit the electromagnetic effect and/or field created when electrical power is supplied.

In some implementations, runners 97 and 97 as depicted in FIG. 9 may share one or more features attributed to runners 16 and 17 in FIGS. 1 and 2, and/or runners 36 and 37 in FIGS. 3 and 4, and/or runners 76 and 77 in FIG. 7, and/or runners 88 and 89 in FIG. 8. For example, runners 97 and 98 in FIG. 9 may include material that is flexible.

Figure 10:
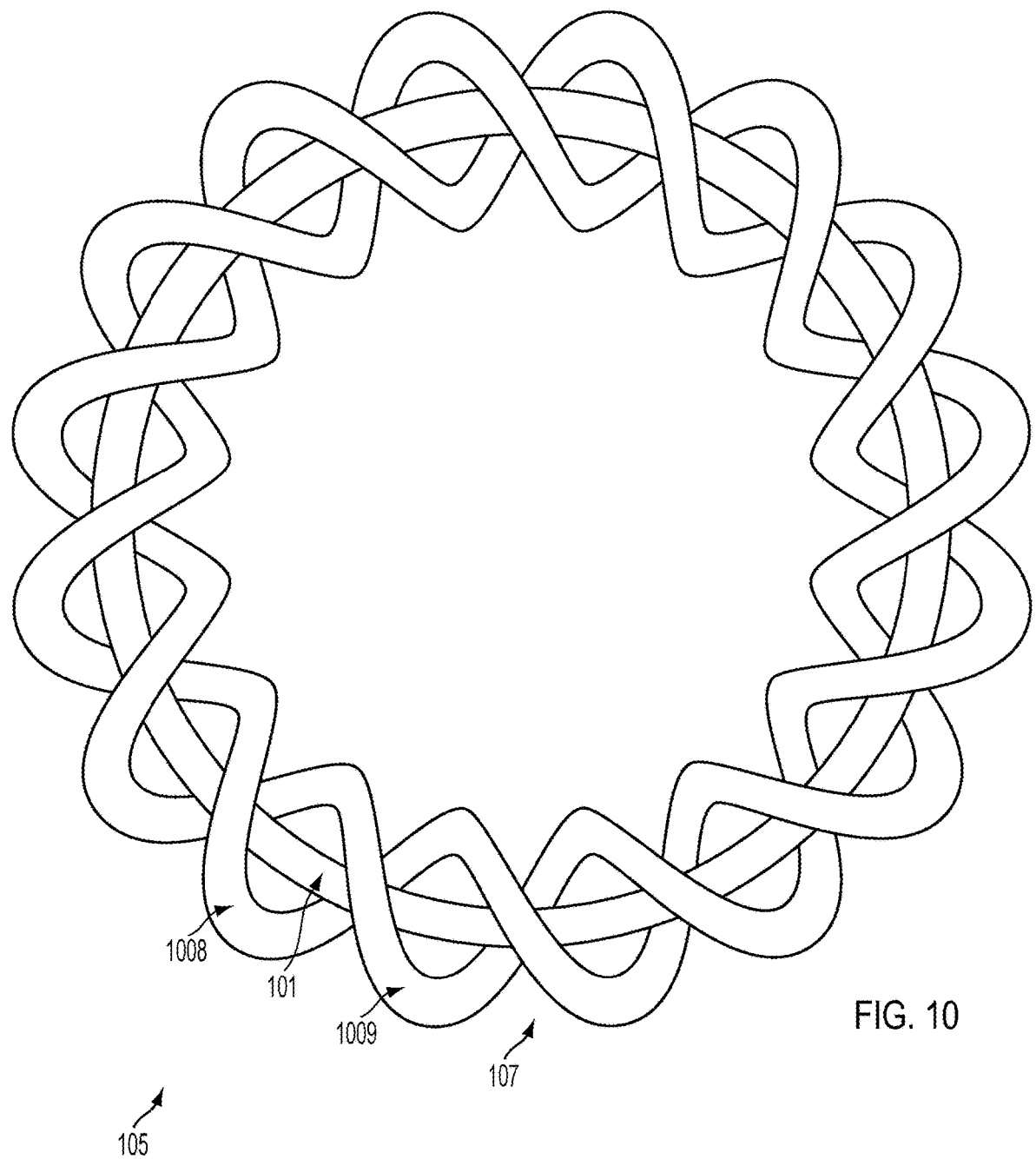
FIG. 10 illustrates a top-down view of an exemplary system combining a body that includes a toroidal structure within a double helix.

FIG. 10 illustrates a top-down view of an exemplary system 105 that combines a body 107 with other components. Body 107 may include two intertwined helically wound runners, runner 1008 and runner 1009, sharing the same circular axis in a similar manner as depicted in, e.g., FIGS. 3, 5, and 8. Runners 1008 and 1009 may be helically wound around a toroidal structure 101 to form (part of) system 105. For example, in some implementations, runners 1008 and/or 1009 may include flexible material. Runner 1008 and runner 1009 may be coupled to toroidal structure 101 by struts (not shown in this view). In some implementations, one or more of runner 1008, runner 1009, and/or toroidal structure 101 may have one or more wires spirally wound therearound (not shown in FIG. 10), e.g. conductive wires that may be used to generate an electromagnetic effect (described in more detail elsewhere in this disclosure). In some implementations, runners 1008 and 1009 as depicted in FIG. 10 may share one or more features attributed to runners 88 and 89 in FIG. 8, runners 16 and 17 in FIGS. 1 and 2, runners 36 and 37 in FIGS. 3 and 4, and/or runners 76 and 77 in FIG. 7. For example, in some implementations, runners 1008 and/or 1009 may include flexible material.

Figure 11A:
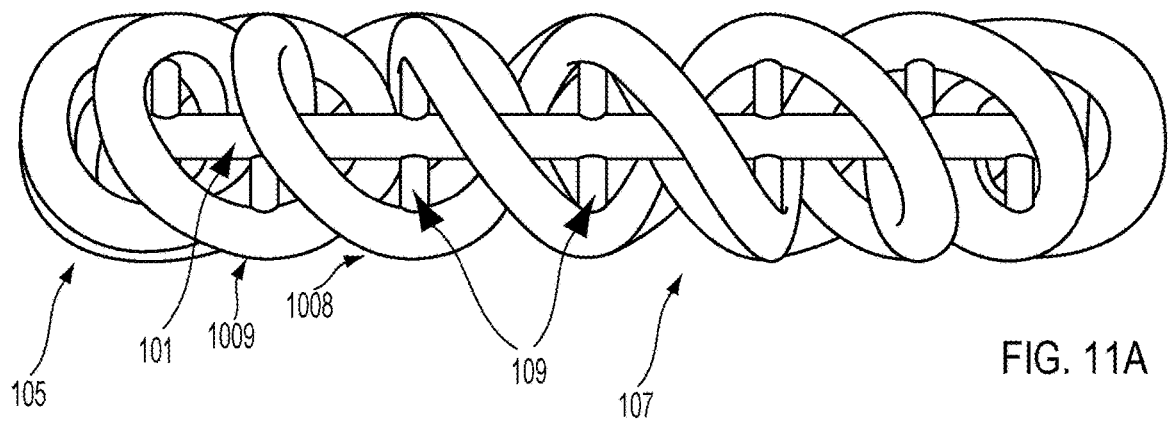
FIG. 11A illustrates a side view of an exemplary system combining a body that includes a toroidal structure within a double helix.

FIG. 11A illustrates a side view of system 105 that combines body 107 with runner 1008 and runner 1009 (as shown in an alternative view in FIG. 10), and/or other components. Body 107 may include struts 109. Struts 109 may be configured to couple one or more of runner 1008 and runner 1009 to toroidal structure 101.

Figure 11B:
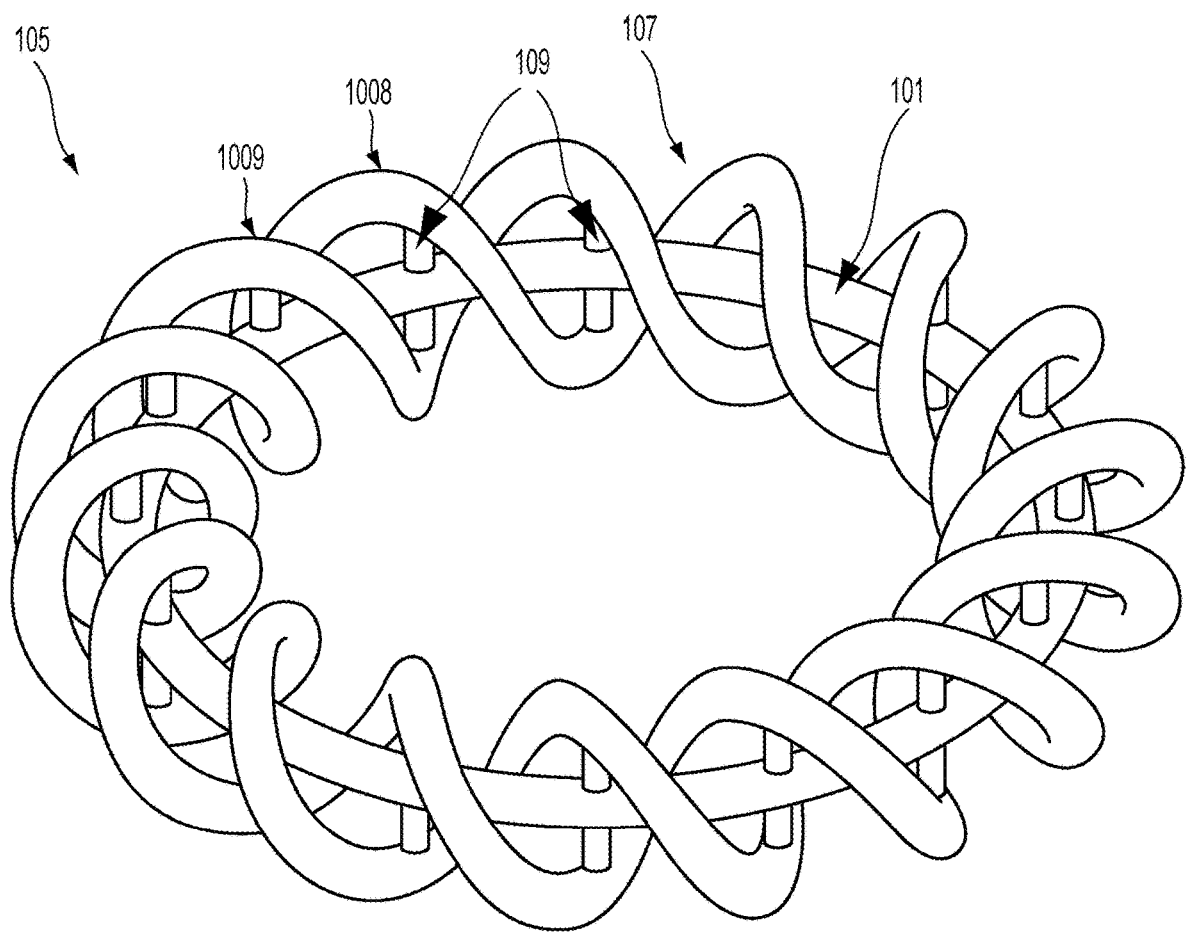
FIG. 11B illustrates an isometric view of an exemplary system combining a body that includes a toroidal structure within a double helix.

FIG. 11B illustrates an isometric view of system 105 that combines body 107 with runner 1008 and runner 1009 (as shown in an alternative view in FIGS. 10 and 11A), and/or other components. Body 107 may include struts 109. Struts 109 may be configured to couple one or more of runner 1008 and runner 1009 to toroidal structure 101.

FIG. 15 illustrates a top-down view of system 1505 that combines body 1507 with runner 1008 and runner 1009 (as shown in an alternative view in FIGS. 10, 11A, and 11B), and/or other components. System 1505 and body 1507 may share one or more features attributed to system 105 and body 107 as depicted in FIGS. 10, 11A, and 11B. Body 1507 may include wires 1501, 1502, and 1503 that are spirally wound around runner 1008, runner 1009, and toroidal structure 101, respectively. Body 1507 may include connectors 1511, 1512, and 1513 that are configured to connect wires 1501, 1502, and 1503, respectively, to one or more current sources (not shown in FIG. 15).

Figure 16:
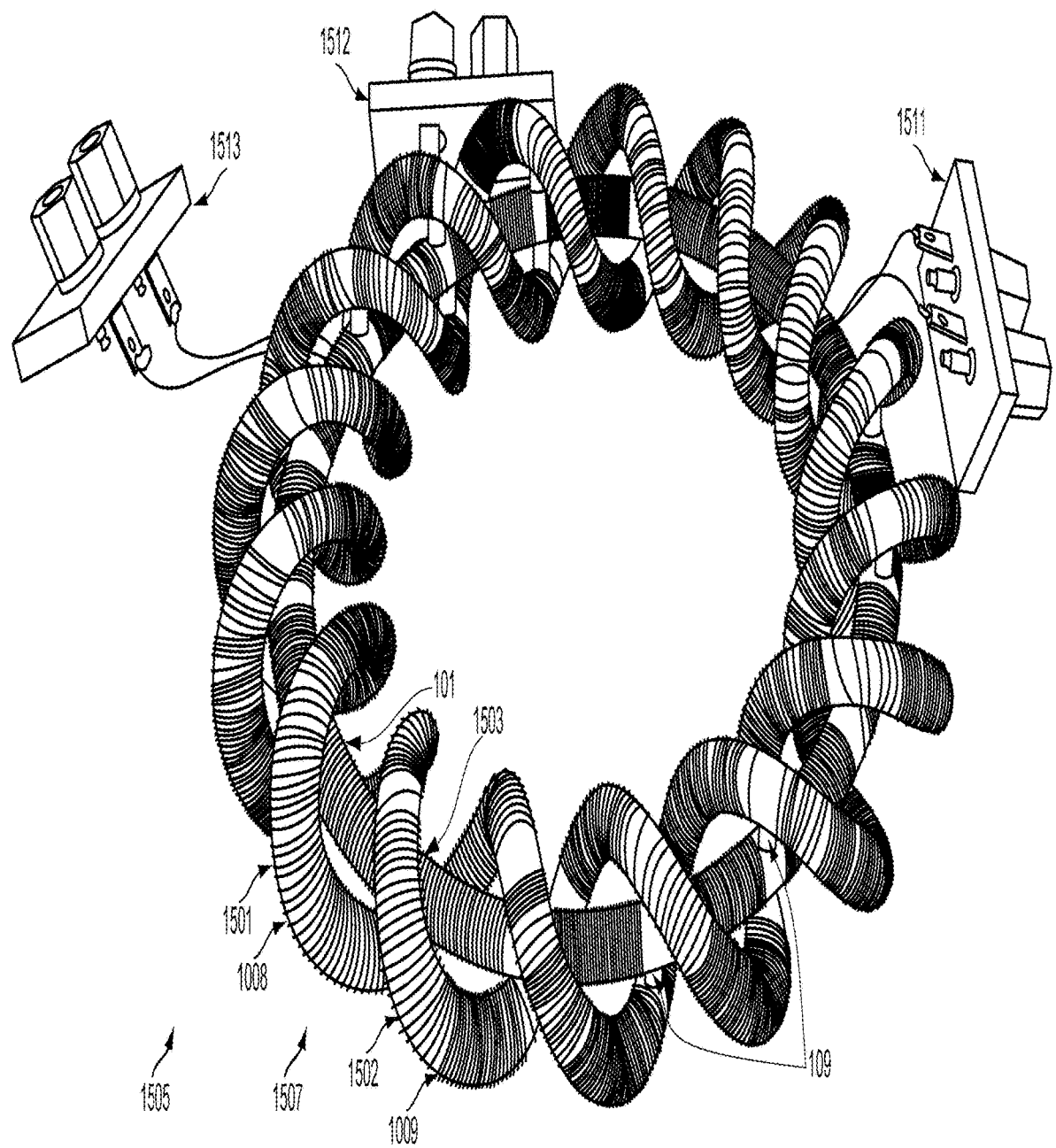
FIG. 16 illustrates an isometric view of an exemplary system combining a body that includes a toroidal structure within a double helix.

FIG. 16 illustrates an isometric view of system 105 that combines body 1507 with runner 1008 and runner 1009 (as shown in an alternative view in FIG. 15), and/or other components. Body 1507 may include wires 1501, 1502, and 1503 that are spirally wound around runner 1008, runner 1009, and toroidal structure 101, respectively. Body 1507 may include connectors 1511, 1512, and 1513 that are configured to connect wires 1501, 1502, and 1503, respectively, to one or more current sources (not shown in FIG. 16). Body 1507 may include struts 109. Struts 109 may be configured to couple one or more of runner 1008 and runner 1009 to toroidal structure 101.

Any of the bodies and/or systems shown in FIGS. 1-10, 11A, 11B, 15, and 16 may be used in an electrical system. Conductive wires may be spirally wound around one or more runners, one or more struts, and/or any combination thereof to produce electrical systems having specific electromagnetic properties when electrical power is supplied to one or more of the conductive wires.

Applications for any of the electrical systems described herein may include affecting growth and/or growth rate of plants and/or other (living) organisms, medical applications, therapeutic applications, energy production, energy conversion, energy transformation, adenosine triphosphate (ATP) production, ATP transfer, ATP processing, and/or other applications. In some implementations, an electrical system including any of these bodies (and/or multiple instances thereof) may be used as a component in an electrical circuit, performing one or more functions and/or applications including a (tunable) inductor, a (Tesla) coil, a transformer, a transducer, a transistor, a resistor, a solenoid, a stator for an electrical motor, an electromagnet, an electromagnetic pulse generator, an electromagnetic actuator, an energy conversion device, a position servomechanism, a generator, a stepping motor, a DC motor, a (contact-free) linear drive, an axial flux device, a measurement device for magnetic permeability, a dipole magnet, and a device to alter electron and/or particle trajectory.

Figure 12:
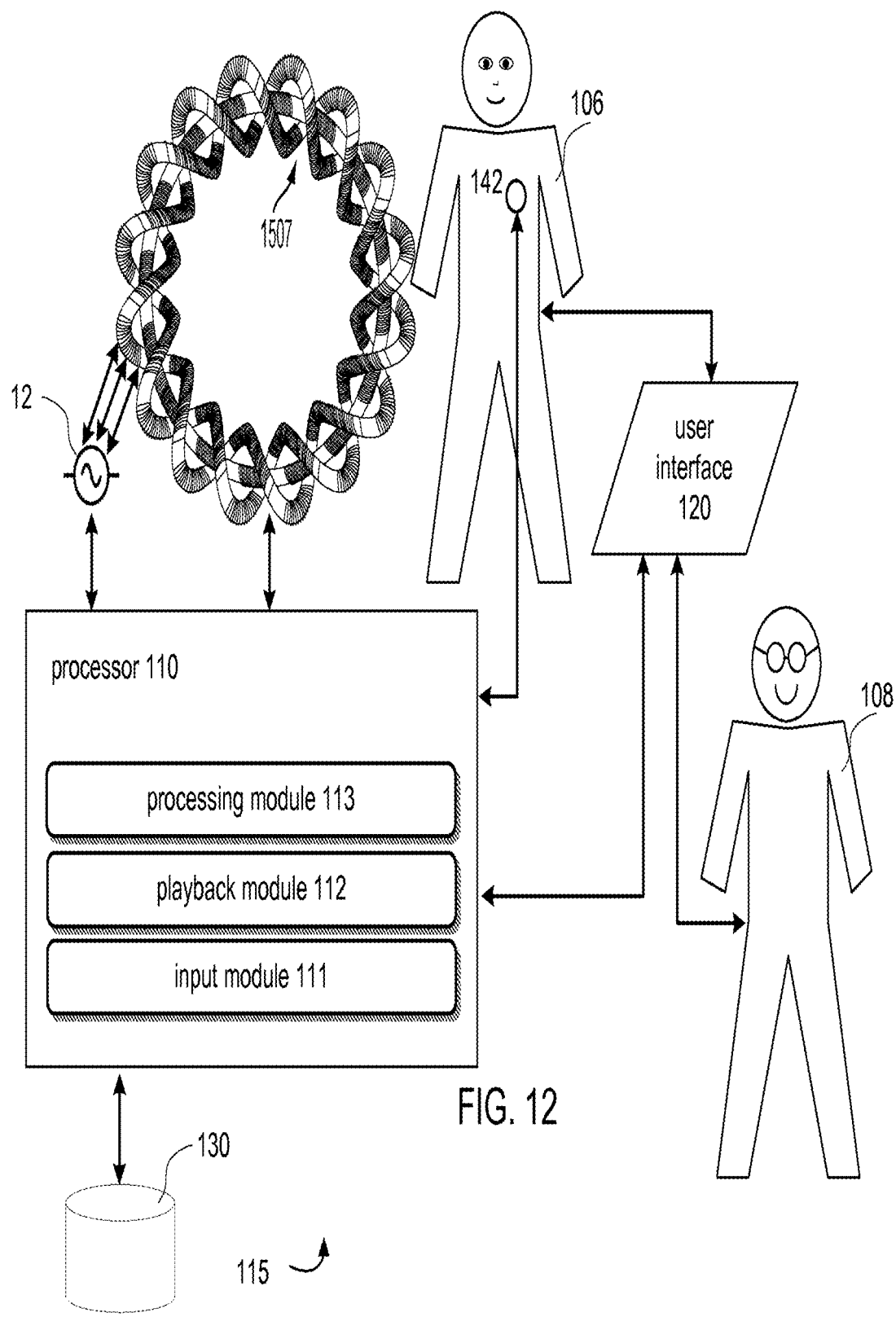
FIG. 12 schematically illustrates a system for providing therapy to a subject, according to one or more implementations.

By way of illustration, FIG. 12 illustrates an electrical system 115 including a body the same as or similar to body 1507 (shown in FIG. 15). In some implementations, body 1507 may include a first runner and a second runner, which may be similar to or the same as runner 1008 and runner 1009 shown in FIG. 15.

Referring to FIG. 12, in some implementations, body 1507 may be arranged in a toroidal shape. Conductive wires may be wound around the runners depicted in FIG. 12. Electrical system 115 may further include one or more of a user interface 120, one or more physical processors 110, one or more sensors 142, electronic storage 130, one or more current sources 12, an input component 111, a playback component 112, a processing component 113, connectors (not shown) and/or other components.

Sensor(s) 142 may be configured to generate output signals conveying information. The information may include electrophysiological information and/or other information. In some implementations, the one or more sensors 142 may include one or more of an audio sensor, a microphone, a stethoscope, a pressure sensor, a motion sensor, a proximity sensor, an electromagnetic sensor, an electrode, a temperature sensor, a current sensor, an optical sensor, an electro-optical sensor, and/or other sensors or combinations thereof. In some implementations, the one or more processors 110 may be configured to provide information-processing capabilities and/or execute computer program components, including but not limited to input component 111, playback component 112, processing component 113, and/or other components. By way of non-limiting example, additional structures and/or features of sensor 142, processor 110, user interface 120, electronic storage 130, input component 111, playback component 112, and/or processing component 113, may be described in U.S. Pat. No. 9,504,844, to Schmidt, entitled "Health Applications for Using Bio-Feedback to Control an Electromagnetic Field," which was filed Feb. 28, 2014, which is hereby incorporated into this disclosure by reference in its entirety. This application may also be referred to as "the '412 application" herein.

The one or more current sources 12 may be configured to induce one or more currents across electrical leads, including but not limited to the electrical leads of the one or more conductive wires wound around the runners and/or the toroidal structure of body 1507. In some implementations, the one or more currents may include one or more alternating currents. In some implementations, one or more induced currents may correspond to one or more sensor-generated output signals. In some implementations, the one or more induced currents may correspond to one or more signals generated by a transducer and/or one or more other components of system 115. In some implementations, the one or more current sources 12 may be configured to induce three independent currents to the three (twisted) wires that are spirally wound around the first runner, second runner, and toroidal structure of body 1507, respectively.

Referring to FIG. 12, in some implementations, the current supplied to the conductive wires wound around the runners of body 1507 may be the same or similar with regard to one or more electrical characteristics, including but not limited to frequency, amplitude, power level, and/or other electrical operating characteristics. In some implementations, one or more electrical characteristics of the currents supplied to the conductive wires wound around the runners and/or the toroidal structure of body 1507 may be different.

In some implementations, an alternating current supplied to body 1507 may include a carrier signal and a modulating signal. In some implementations, carrier signals used for the alternating current may be radio-frequency signals. As used herein, radio frequency may refer to frequencies between about 30 kHz and about 30 GHz. In some implementations, the modulating signal for the alternating current may be modulated through one or more of amplitude modulation, frequency modulation, phase modulation, digital modulation, and/or other types of modulation.

In some implementations, the one or more frequencies included in the alternating current may be based on audio recordings of a note, tone, or chord, generated by a frequency generator and/or a (musical) instrument. In some implementations, a first frequency may be used for the first runner, a second frequency may be used for the second runner, and a third frequency may be used for the toroidal structure of body 1507. For example, a first frequency may be based on the sound of an instrument, e.g. a piano, playing an A above middle C (also referred to as A4, which may include sound having a frequency of about 432 Hz, depending on the tuning system used). For example, a second frequency may be based on the sound of some instrument, e.g. a piano, playing a note forming a harmonious interval with A4, e.g. E5, which may include sound having a frequency of about 648 Hz. For example, a third frequency may be based on the sound of some instrument, e.g. a piano, playing a note forming a harmonious interval with A4, e.g. A5, which may include sound having a frequency of about 864 Hz. The particular tuning used in some implementations may be referred to as Pythagorean tuning. Mathematically perfect tuning may combine notes having a 3:2 ratio. Different types of tuning (or tuning systems), including but not limited to equal tempered tuning, may be used and considered within the scope of this disclosure.

Processor 110 may include one or more of a digital processor, an analog processor, a digital circuit designed to process information, a central processing unit, a graphics processing unit, an analog circuit designed to process information, and/or other mechanisms for electronically processing information. Although processor 110 is shown in FIG. 12 as a single entity, this is for illustrative purposes only. In some implementations, processor 110 may include a plurality of processing units.

It should be appreciated that although components 111-113 are illustrated in FIG. 12 as being co-located within a single processing unit, in implementations in which processor 110 includes multiple processing units, one or more of components 111-113 may be located remotely from the other components. The description of the functionality provided by the different components 111-113 described herein is for illustrative purposes, and is not intended to be limiting, as any of components 111-113 may provide more or less functionality than is described. For example, one or more of components 111-113 may be eliminated, and some or all of its functionality may be incorporated, shared, integrated into, and/or otherwise provided by other ones of components 111-113. Note that processor 110 may be configured to execute one or more additional components that may perform some or all of the functionality attributed below to one of components 111-113.

Input component 111 may be configured to obtain information, e.g. from one or more digital audio files, or, alternatively and/or simultaneously, based on sensor-generate output signals. In some implementations, the information may be obtained from storage, e.g. from electronic storage. Information obtained from storage may include electronic audio files in any format, including but not limited to MP3, WMA, WAV, AIFF, and/or other audio formats. In some implementations, information may be obtained from sound sources including frequency generators, phonographs, CD-players, DVD players, AM radio, FM radio, and/or other sound sources.

Processing component 113 may be configured to process the obtained information from input component 111. In some implementations, processing component 113 may be configured to generate a processed signal based on the obtained information from input component 111. For example, processing module 113 may convert, filter, modify, and/or otherwise transform information or signals from input module 111 to generate the processed signal.

Playback component 112 may be configured to produce sound signals based on one or more of the obtained information from input component 111 and/or the processed signal from processing component 113. The sound signals produced by playback component 112 may be coupled electrically to the leads of one or more conductive wires wound around one or more runners of body 1110 such that the induced current corresponds to and/or is based on the sound signals. Alternatively, and/or simultaneously, the induced current may be controlled by and/or based on the sound signals produced by playback component 112. In some implementations, the sound signals produced by playback module 112 may be amplified by an amplifier before being electrically coupled to the leads of one or more conductive wires. In some preferred implementations, the amplifier may be an audio amplifier ranging between 100 W and 400 W. Other types of amplifiers and/or amplifiers having a different power range are also contemplated.

Figure 14A:
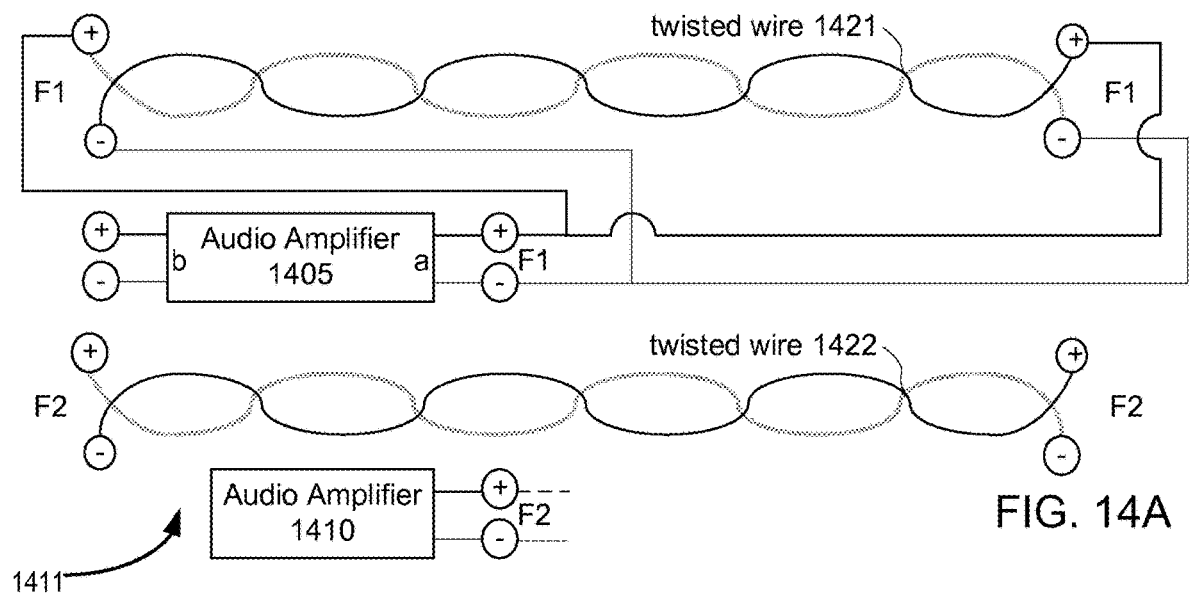
FIGS. 14A and 14B illustrate wiring diagrams for wiring wires around runners, according to one or more implementations.

FIG. 14A illustrates a wiring diagram 1411 for wiring a twisted wire 1421 and/or a twisted wire 1422 around one or more runners of a body having two or more intertwined helically wound runners, as described elsewhere in this disclosure. Any of the windings disclosed herein may be used for a body having a toroidal structure as shown in FIG. 15. Referring to FIG. 14A, in some implementations, twisted wire 1421 may be wound around a first runner (e.g. the same as or similar to runner 88 shown in FIG. 8 or runner 1008 in FIG. 15). One or more signals may be provided to twisted wire 1421 through four leads (indicated by a circled positive or negative sign in FIG. 14A). The signal provided to twisted wire 1421 may be based on audio recordings of a note, tone, or chord, generated by a frequency generator, a (musical) instrument, and/or another sound source. By way of non-limiting example, the signal may be similar to or based on the information obtained by an input component (e.g. the same as or similar to input component 111 shown in FIG. 12), the processed signal generated by a processing component (e.g. the same as or similar to processing component 113 shown in FIG. 2), a sound signal produced by a playback component (e.g. the same as or similar to playback component 112 shown in FIG. 12), and/or an amplified signal from an audio amplifier 1405. In some implementations, audio amplifier 1405 may support multiple audio channels, e.g. a channel "a" and a channel "b" as illustrated by labels "a" and "b" in FIG. 14A. The signal on channel "a" of audio amplifier 1405 is labeled "F1." In some implementations, signal F1 may substantially include and/or be based on a particular frequency. As shown in FIG. 14A, the positive side of signal F1 may be electrically and/or operationally connected to two of the four leads of twisted wire 1421, wherein the two selected leads are on opposite ends of twisted wire 1421. The negative side of signal F1 may be electrically and/or operationally connected to the remaining two of the four leads of twisted wire 1421, which may be on opposite ends of twisted wire 1421.

In some implementations, wiring diagram 1411 may include a second twisted wire 1422. In some implementations, twisted wire 1422 may be wound around a second runner (e.g. the same as or similar to runner 89 shown in FIG. 8 or runner 1009 in FIG. 15). One or more signals may be provided to twisted wire 1422 through four leads (indicated by a circled positive or negative sign in FIG. 14A). The signal provided to twisted wire 1422 may, in some implementations, be the same as the signals provided to twisted wire 1421, e.g. the F1 signal. In some implementations, the signal provided to twisted wire 1422 may be provided by channel "b" of audio amplifier 1405. In some implementations, the signal provided to twisted wire 1422 may be provided by one or more channels of an audio amplifier 1410. The signal of audio amplifier 1410 is labeled "F2." In some implementations, signal F2 may substantially include and/or be based on a particular frequency, which may be a different frequency than the frequency used for signal F1. For example, signal F1 may be based on a frequency of 250 Hz, and signal F2 may be based on a frequency of four times the frequency of signal F1, e.g. 1000 Hz. Likewise, signals F1 and F2 may be 216 Hz and 864 Hz, respectively, by way of non-limiting example. As indicated in FIG. 14A, the positive side of signal F2 may be electrically and/or operationally connected the two positive leads of twisted wire 1422, on opposite ends of twisted wire 1422. The negative side of signal F1 may be electrically and/or operationally connected to the two negative leads of twisted wire 1422, on opposite ends of twisted wire 1422.

Figure 14B:
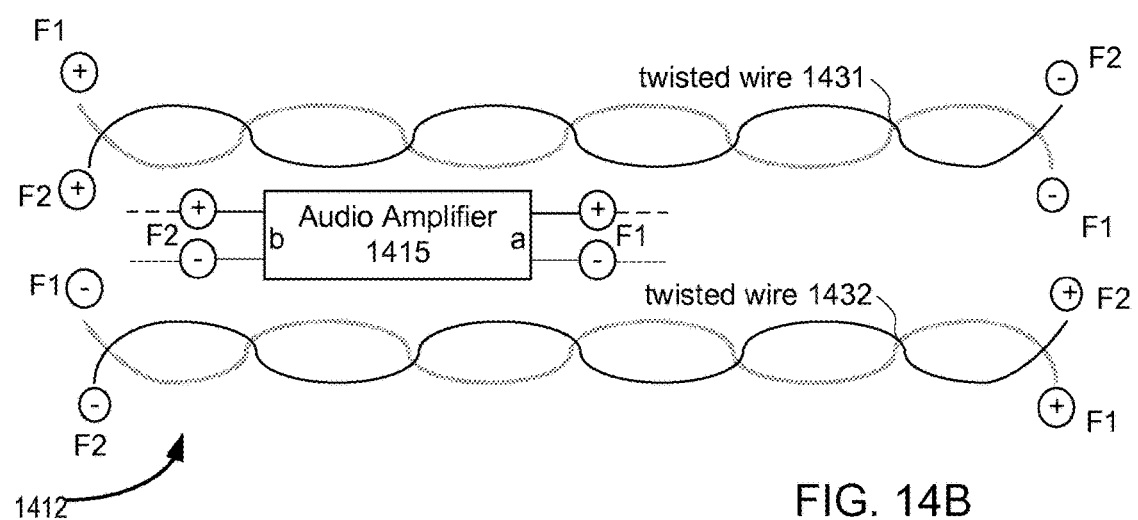

FIG. 14B illustrates a wiring diagram 1412 for wiring a twisted wire 1431 and a twisted wire 1432 around two runners of a body having two intertwined helically wound runners, as described elsewhere in this disclosure. In some implementations, twisted wire 1431 may be wound around a first runner (e.g. the same as or similar to runner 88 shown in FIG. 8 or runner 1008 in FIG. 15). In some implementations, twisted wire 1432 may be wound around a second runner (e.g. the same as or similar to runner 89 shown in FIG. 8 or runner 1009 in FIG. 15). One or more signals may be provided to twisted wire 1431 through four leads and to twisted wire 1432 through four leads (indicated by a circled positive or negative sign in FIG. 14B). In some implementations, the signals provided to twisted wire 1431 and 1432 may be provided by an audio amplifier 1415 that supports multiple audio channels, e.g. a channel "a" and a channel "b" as illustrated by labels "a" and "b" in FIG. 14B. The signal on channel "a" of audio amplifier 1415 is labeled "F1." The signal on channel "b" of audio amplifier 1415 is labeled "F2." As shown in FIG. 14B, the positive side of signal F1 may be electrically and/or operationally connected to two of the eight leads of twisted wires 1431 and 1432, wherein the two selected leads are on opposite ends. The negative side of signal F1 may be electrically and/or operationally connected to two other leads of twisted wires 1431 and 1432, which may be on opposite ends of twisted wire 1421. As shown in FIG. 14B, the positive side of signal F2 may be electrically and/or operationally connected to two of the eight leads of twisted wires 1431 and 1432, wherein the two selected leads are on opposite ends. The negative side of signal F2 may be electrically and/or operationally connected to two other leads of twisted wires 1431 and 1432, which may be on opposite ends of twisted wire 1421. In some implementations using wiring diagram 1412, signal F1 may be based on a frequency of 250 Hz, and signal F2 may be based on a frequency of four times the frequency of signal F1, e.g. 1000 Hz. Likewise, signals F1 and F2 may be 216 Hz and 864 Hz, respectively, by way of non-limiting example.

In some implementations, the wiring of two twisted wires around two intertwined helically wound runners as shown in wiring diagram 1411 and/or wiring diagram 1412 may be used as a basis for wiring an electrical system having two, three, or more bodies arranged in each other's proximity. Such an electrical system may be the same as or similar to system 105 shown in FIG. 10 or system 1505 shown in FIG. 15. For example, in an electrical system using two bodies that each include two intertwined helically wound runners, the four runners may be wound with four twisted wires having a total of 16 leads that may be used to electrically and/or operationally connect to 1, 2, and/or 4 audio amplifiers and/or channels thereof that are the same as or similar to audio amplifier 1405, audio amplifier 1410, and/or audio amplifier 1415 (e.g. using channels "a" and "b").

Electronic storage 130 of system 115 in FIG. 12 comprises electronic storage media that electronically stores information. The electronic storage media of electronic storage 130 may include one or both of system storage that is provided integrally (i.e., substantially non-removable) with system 115 and/or removable storage that is connectable to system 115 via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 115 to function properly. For example, electronic storage 130 may store sound information and/or electronic audio files (as discussed elsewhere herein), and/or other information. Electronic storage 130 may be a separate component within system 115, or electronic storage 130 may be provided integrally with one or more other components of system 115 (e.g., processor 110).

User interface 120 of system 115 in FIG. 12 is configured to provide an interface between system 115 and a user (e.g., a user 108, a subject 106, a caregiver, a therapy decision-maker, etc.) through which the user can provide information to and receive information from system 115. This enables data, results, and/or instructions and any other communicable items, collectively referred to as "information," to be communicated between the user and system 115. An example of information that may be conveyed to user 108 is an indication of the volume and/or intensity of the sound signals produced by playback module 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one implementation, user interface 120 may be integrated with a removable storage interface provided by electronic storage 130. In this example, information is loaded into system 115 from removable storage (e.g., a smart card, a flash drive, a removable disk, etc.) that enables the user(s) to customize system 115. Other exemplary input devices and techniques adapted for use with system 115 as user interface 120 include, but are not limited to, an RS-232 port, RF link, an IR link, modem (telephone, cable, Ethernet, internet or other). In short, any technique for communicating information with system 115 is contemplated as user interface 120.

Figure 13:
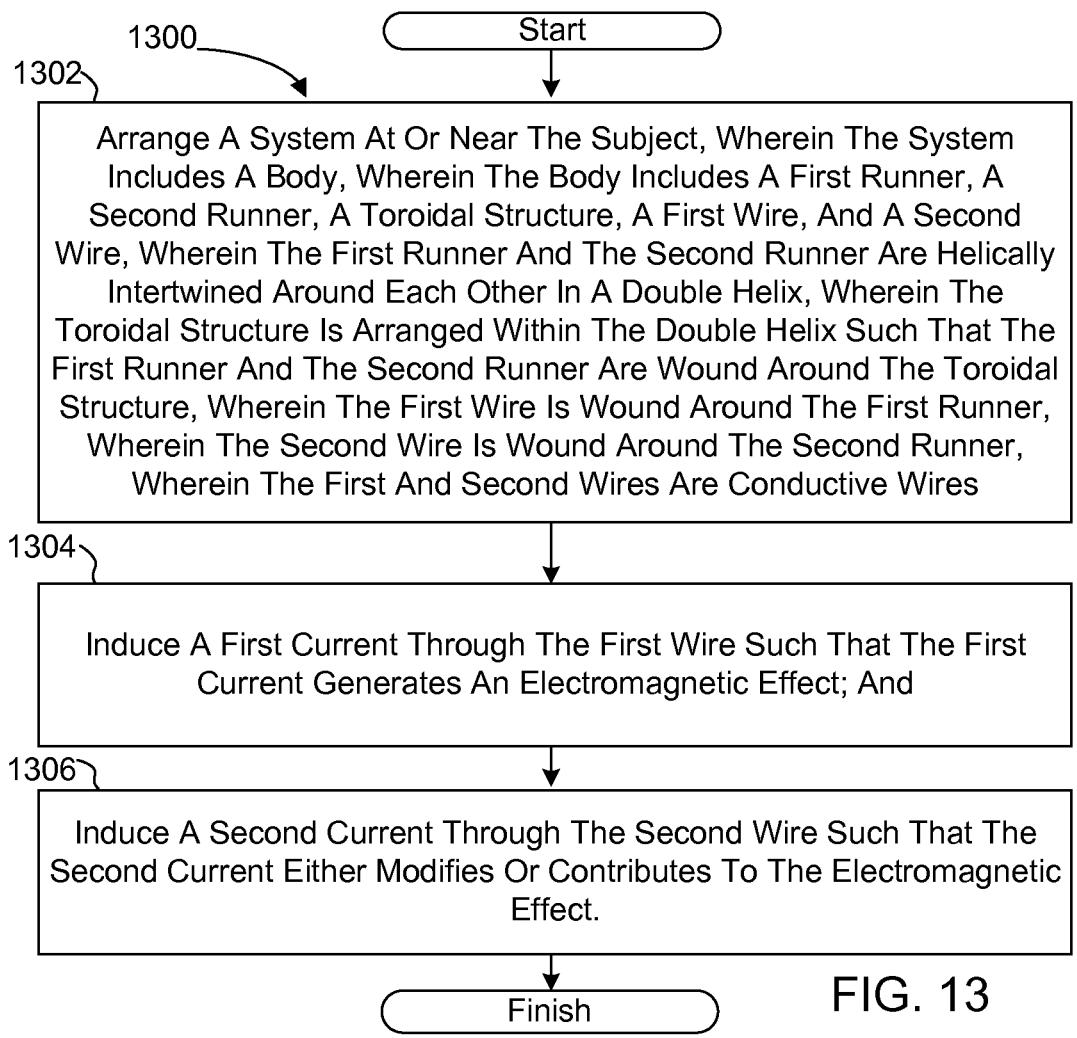
FIG. 13 illustrates a method for providing therapy to a subject, according to one or more implementations.

FIG. 13 illustrates a method 1300 for providing therapy and/or electromagnetic effects to a subject. The operations of method 1300 presented below are intended to be illustrative. In certain implementations, method 1300 may be accomplished with one or more additional operations not described, and/or without one or more of the operations discussed. Additionally, the order in which the operations of method 1300 are illustrated in FIG. 13 and described below is not intended to be limiting.

In certain implementations, method 1300 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 1300 in response to instructions stored electronically on an electronic storage medium. The one or more processing devices may include one or more devices configured through hardware, firmware, and/or software to be specifically designed for execution of one or more of the operations of method 1300.

Regarding method 1300, at an operation 1302, a system is arranged at or near the subject. The system includes a body. The body includes a first runner, a second runner, a toroidal structure, a first wire, and a second wire. The first runner and the second runner are helically intertwined around each other in a double helix. The toroidal structure is arranged within the double helix such that the first runner and the second runner are wound around the toroidal structure. The first wire is wound around the first runner. The second wire is wound around the second runner. The first and second wires are conductive wires. In some implementations, operation 1302 is performed by a system and/or body the same as or similar to system 105 and body 107 (shown in FIGS. 10 and 15 and described herein).

At an operation 1304, a first current is induced through the first wire such that the first current generates an electromagnetic effect. In some implementations, operation 1304 is performed by and/or through a connector and/or a current source the same as or similar to connector 1501 and/or current source 12 (shown in FIGS. 15 and 12 and described herein).

At an operation 1306, a second current is induced through the second wire such that the second current either modifies or contributes to the electromagnetic effect. In some implementations, operation 1306 is performed by and/or through a connector and/or a current source the same as or similar to connector 1502 and/or current source 12 (shown in FIGS. 15 and 12 and described herein).

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any implementation can be combined with one or more features of any other implementation.

What is claimed is:

1. A system comprising:
    a body, wherein the body comprises
        a first runner and a second runner that are intertwined and helically wound around each other in a double helix;
        a first conductor wound around the first runner,
            wherein the first conductor includes a first pair of conductive wires, and
            wherein the first pair of conductive wires includes a first wire and a second wire;
        a second conductor wound around the second runner,
            wherein the second conductor includes a second pair of conductive wires, and
            wherein the second pair of conductive wires includes a third wire and a fourth wire;
        a toroidal structure arranged within the double helix,
            wherein the toroidal structure is a continuously uninterrupted round structure,
            wherein the first runner and the second runner are wound around the toroidal structure, and
        a fifth wire wound around the toroidal structure,
            wherein the fifth wire is a conductive wire; and
    one or more current sources that provide
        a first alternating current to the first wire and the second wire,
        a second alternating current to the third wire and the fourth wire, and,
        a third current to the fifth wire;
    wherein the system is configured to generate an electromagnetic effect responsive to the first alternating current and the second alternating current being provided.

2. The system of claim 1, wherein the first wire and the second wire are a twisted pair.

3. The system of claim 1, wherein the third wire and the fourth wire are a twisted pair.

4. The system of claim 1, wherein the system is further configured to provide therapy to a subject in proximity to the body, wherein the therapy is provided through the electromagnetic effect.

5. The system of claim 4, further comprising a sensor configured to generate output signals conveying information related to electrophysiological information of the subject, wherein the one or more current sources are configured to dynamically control at least one of the first alternating current and the second alternating current to correspond to the output signals.

6. The system of claim 4, wherein the therapy interacts with an infrared field around the subject.

7. The system of claim 4, wherein the therapy interacts with a flow of energy of the subject.

8. The system of claim 1, wherein the system is further configured to promote growth of a living organism disposed within or near the body of the system.

9. The system of claim 1, wherein at least one of the first alternating current and the second alternating current comprises one or more frequencies between 0 Hz and 20 kHz.

10. The system of claim 1, wherein at least one of the first alternating current and the second alternating current comprises one or more frequencies in a range of human-perceptible auditory sensitivity.

11. The system of claim 10, further comprising
    one or more physical processors configured via computer-readable instructions to obtain information that includes one or more digital audio files,
        process the information and generate a processed signal based on the information, and produce sound signals based on the processed signal,
    wherein the one or more current sources are configured to dynamically control at least one of the first alternating current and the second alternating current to correspond to the sound signals, wherein the one or more frequencies included in the first alternating current and the second alternating current correspond to one or more frequencies of the sound signals.

12. The system of claim 1, wherein the first alternating current comprises a first frequency, wherein the second alternating current comprises a second frequency, and wherein the first frequency and the second frequency form a harmonious interval.

13. The system of claim 1, wherein the first alternating current comprises a first frequency, wherein the second alternating current comprises a second frequency, and wherein the first frequency and second frequency form intervals having small-integer ratios.

14. The system of claim 1, wherein the first alternating current and the second alternating current flow in a similar direction around the body.

15. The system of claim 1, wherein the first alternating current and the second alternating current flow in an opposite direction around the body.

16. The system of claim 1, wherein the electromagnetic effect includes an electromagnetic field.

17. A method for providing an electromagnetic effect, the method comprising:
arranging a system at or near a subject, wherein the system comprises
a body, wherein the body comprises
a first runner and a second runner that are intertwined and helically wound around each other in a double helix,
a first conductor wound around the first runner,
wherein the first conductor includes a first pair of conductive wires, and
wherein the first pair of conductive wires includes a first wire and a second wire, and
a second conductor wound around the second runner,
wherein the second conductor includes a second pair of conductive wires, and
wherein the second pair of conductive wires includes a third wire and a fourth wire, and
a toroidal structure arranged within the double helix,
wherein the toroidal structure is a continuously uninterrupted round structure,
wherein the first runner and the second runner are wound around the toroidal structure, and,
a fifth wire wound around the toroidal structure,
wherein the fifth wire is a conductive wire, and,
one or more current sources;
providing
a first alternating current to the first wire and the second wire via said one or more current sources,
a second alternating current to the third wire and the fourth wire via said one or more current sources, and
a third current to the fifth wire; and,
generating said electromagnetic effect via said system responsive to the first alternating current and the second alternating current being provided.

18. The method of claim 17, wherein the first wire and the second wire are a first twisted pair, and wherein the third wire and the fourth wire are a second twisted pair.

19. The method of claim 17, wherein at least one of the first alternating current and the second alternating current comprises one or more frequencies in a range of human-perceptible auditory sensitivity.

20. The method of claim 19, further comprising
obtaining information that includes one or more digital audio files via one or more physical processors configured via computer-readable instructions, wherein said system further comprises said one or more physical processors;
processing the information and generating a processed signal based on the information via said one or more physical processors configured via said computer-readable instructions;
producing sound signals based on the processed signal via said one or more physical processors configured via said computer-readable instruction; and,
dynamically controlling at least one of the first alternating current and the second alternating current to correspond to the sound signals via the one or more current sources, wherein the one or more frequencies included in the first alternating current and the second alternating current correspond to one or more frequencies of the sound signals.

* * * * *